(12) United States Patent
Mielnik et al.

(10) Patent No.: US 9,802,726 B2
(45) Date of Patent: Oct. 31, 2017

(54) BOTTLE DECONTAMINATION SYSTEM

(71) Applicant: American Sterilizer Company, Mentor, OH (US)

(72) Inventors: Thaddeus J Mielnik, Concord, OH (US); Aaron L Hill, Erie, PA (US)

(73) Assignee: American Sterilizer Company, Mentor, OH (US)

( * ) Notice: Subject to any disclaimer, the term of this patent is extended or adjusted under 35 U.S.C. 154(b) by 787 days.

(21) Appl. No.: 14/095,146

(22) Filed: Dec. 3, 2013

(65) Prior Publication Data

US 2014/0083051 A1 Mar. 27, 2014

Related U.S. Application Data

(62) Division of application No. 12/892,453, filed on Sep. 28, 2010, now Pat. No. 8,621,824.

(Continued)

(51) Int. Cl.
| | | |
|---|---|---|
| *B65B 55/10* | (2006.01) | |
| *B65B 55/18* | (2006.01) | |

(Continued)

(52) U.S. Cl.
CPC ............. *B65B 55/18* (2013.01); *A61L 2/208* (2013.01); *B65B 55/02* (2013.01); *B65B 55/10* (2013.01)

(58) Field of Classification Search
CPC ........ B65B 55/10; B65B 55/18; B65B 55/02; A61L 2/208
See application file for complete search history.

(56) References Cited

U.S. PATENT DOCUMENTS

| | | | |
|---|---|---|---|
| 2,590,556 A | 3/1952 | Marchadour | 226/19 |
| 2,824,344 A | 2/1958 | Abrams | 21/80 |

(Continued)

FOREIGN PATENT DOCUMENTS

| | | | |
|---|---|---|---|
| CN | 101237893 | 8/2008 | ............... A61L 2/20 |
| DE | 196 42 987 A1 | 4/1998 | ............. B65B 55/04 |

(Continued)

OTHER PUBLICATIONS

Krones to Unveil New Aseptic Sterilisation Process, Press Release obtained from website www.foodproductiondaily.com, Oct. 27, 2008.

(Continued)

*Primary Examiner* — Andrew M Tecco
(74) *Attorney, Agent, or Firm* — Kusner & Jaffe; Michael A. Centanni

(57) ABSTRACT

A system for sterilizing bottles with a gaseous sterilant. The system includes moving means for continuously moving bottles one after another along a path. An assembly is provided for distributing a predetermined amount of the gaseous sterilant from a source of gaseous sterilant to each of the bottles. The assembly includes a plurality of injectors that are movable with the bottles. One of the plurality of injectors is associated with each of the bottles. The injector is fluidly connected to the source of gaseous sterilant when the bottle associated with the injector is disposed along a first portion of the path. The injector is disposed above the bottle when the injector is in a first position. The injector is disposed within an interior of the bottle when the injector is in a second position such that the predetermined amount of the gaseous sterilant is conveyed into the interior of the bottle.

3 Claims, 14 Drawing Sheets

Related U.S. Application Data

(60) Provisional application No. 61/246,752, filed on Sep. 29, 2009.

(51) Int. Cl.
  *A61L 2/20* (2006.01)
  *B65B 55/02* (2006.01)

(56) References Cited

U.S. PATENT DOCUMENTS

| | | | |
|---|---|---|---|
| 3,018,184 A | 1/1962 | Martin | 99/182 |
| 3,606,997 A | 9/1971 | Guckel | 21/56 |
| 5,053,196 A | 10/1991 | Ide et al. | 422/28 |
| 5,558,135 A | 9/1996 | Kronseder et al. | 141/6 |
| 5,848,515 A | 12/1998 | Catelli et al. | 53/167 |
| 6,120,730 A * | 9/2000 | Palaniappan | B65B 55/025 422/28 |
| 6,536,188 B1 | 3/2003 | Taggart | 53/425 |
| 6,752,959 B2 | 6/2004 | Smith et al. | 422/28 |
| 6,919,043 B2 * | 7/2005 | Hayakawa | A61L 2/04 422/28 |
| 7,186,374 B2 | 3/2007 | Zelina et al. | 422/28 |
| 7,341,079 B2 | 3/2008 | Zanga | 141/92 |
| 7,497,237 B2 * | 3/2009 | Till | A61L 2/22 141/11 |
| 8,591,826 B2 * | 11/2013 | Auer | B65B 55/025 422/300 |
| 8,621,824 B2 * | 1/2014 | Mielnik | A61L 2/208 422/28 |
| 2003/0165400 A1 * | 9/2003 | Hayakawa | A61L 2/04 422/28 |
| 2004/0208781 A1 * | 10/2004 | Hayashi | A61L 2/06 422/28 |
| 2005/0226796 A1 * | 10/2005 | Hayakawa | B65B 55/10 422/302 |
| 2006/0005896 A1 * | 1/2006 | Till | B65B 55/10 141/147 |
| 2007/0193652 A1 | 8/2007 | Till et al. | 141/144 |
| 2007/0253859 A1 * | 11/2007 | Hill | A61L 2/208 422/3 |
| 2008/0032059 A1 | 2/2008 | Zimmerer et al. | 427/458 |
| 2008/0152538 A1 | 6/2008 | Quetel et al. | 422/28 |
| 2009/0045350 A1 | 2/2009 | Humele et al. | 250/455.1 |
| 2009/0129975 A1 * | 5/2009 | Colato | A61L 2/208 422/38 |
| 2009/0293429 A1 | 12/2009 | Till | 53/425 |
| 2011/0072759 A1 * | 3/2011 | Mielnik | A61L 2/208 53/167 |

FOREIGN PATENT DOCUMENTS

| | | | | |
|---|---|---|---|---|
| DE | WO 2007036492 A1 * | 4/2007 | | B65B 55/025 |
| GB | 537674 | 7/1941 | | B67B 3/02 |
| GB | 537674 A * | 7/1941 | | B67B 3/02 |
| GB | 740480 | 11/1955 | | |
| GB | 740480 A * | 11/1955 | | B67C 3/10 |
| WO | WO2006/128884 | 12/2006 | | A61L 2/20 |
| WO | WO2006128884 A2 * | 12/2006 | | A61L 2/208 |
| WO | WO 2007/140883 | 12/2007 | | B65B 55/08 |

OTHER PUBLICATIONS

Krones, PET Asept System D—a basis for filling UHT milk products, product information obtained from website www.krones.com, Oct. 27, 2008.

Krones, PET Asept D system for UHT dairy products, product information obtained from website www.krones.com, Oct. 27, 2008.

Krones, Dry Sterilization Process for PET Containers helps Krones Hoist Aseptic Market Growth, Press Release obtained from website www.packstrat.com, May 30, 2007.

* cited by examiner

BOTTLE DECONTAMINATION SYSTEM

RELATED APPLICATIONS

The present application is a divisional of U.S. application Ser. No. 12/892,453, filed Sep. 28, 2010, which claims the benefit of U.S. Provisional Application No. 61/246,752, filed Sep. 29, 2009, said patent applications fully incorporated herein by reference.

FIELD OF THE INVENTION

The present invention relates generally to sterilization processes using a vaporized sterilant, and more particularly, to a system for decontaminating bottles and the like using vaporized hydrogen peroxide and a method of operating the same.

BACKGROUND OF THE INVENTION

Polyethylene terephthalate (PET) bottles are commonly used in the United States as containers for beverages. Prior to filling a bottle with a liquid beverage for human consumption, the bottles undergo a sterilization process.

One method of sterilizing bottles as part of a continuous bottling system is to use liquid sterilant, wherein the bottles are filled with liquid sterilant to sterilize the interior of the bottle, and then rinsed to remove any excess or residual sterilant. Filling and removing a sterilant and rinse solution from a bottle requires that the bottles be repeatedly inverted and returned to an upright position. Rotating bottles from an upright position to an upside down position and vice versa increases the complexity and cost of a continuous bottling system.

Moreover, bottles are typically rinsed with sterilized water, which requires a system for generating the sterile water. Sterile water is expensive to produce, and the sterility level of the water is always suspect.

Another method of sterilizing bottles uses condensed hydrogen peroxide ($H_2O_2$). In these systems, the $H_2O_2$ is first vaporized and then condensed onto the cooler surface of the bottles. The $H_2O_2$ sterilant is typically a mixture of water and hydrogen peroxide. A problem with using condensed vaporized hydrogen peroxide (VHP) systems is that it is difficult to obtain uniform condensation coverage on complex bottle surfaces that may have temperature gradients there along. It is also difficult to determine the concentration of concentrated vaporized hydrogen peroxide that is necessary to reach the condensation point due to variations in both bottle temperature and humidity levels.

The present invention overcomes these and other problems and provides a system for decontaminating bottles and the like as part of a continuous bottle-filling system, wherein a centralized vaporized hydrogen peroxide system provides and controls the concentration of VHP to a bottling system.

SUMMARY OF THE INVENTION

In accordance with a preferred embodiment of the present invention, there is provided a system for decontaminating bottles and the like as part of a continuous bottle-filling system. The system includes moving means for continuously moving bottles one after another along a path. Each of the bottles has an interior. A sterilant feed conduit is connected at one end to a source of gaseous sterilant of a predetermined concentration. A conveying means is provided to convey the gaseous sterilant along the sterilant feed conduit. An assembly is provided for distributing a predetermined amount of the gaseous sterilant from the source of gaseous sterilant to each of the bottles when the bottles are disposed along a first portion of the path. The assembly includes a plurality of injectors that are movable with the bottles. One of the plurality of injectors is associated with each of the bottles as the bottle moves along the first portion of the path. The injector is fluidly connected to the source of gaseous sterilant when the bottle associated with the injector is disposed along the first portion of the path such that the predetermined amount of the gaseous sterilant is conveyed around the bottle and into the interior of the bottle. The injector is movable between a first position and a second position relative to the bottle as the bottle moves along the path. The injector is disposed above the bottle when the injector is in the first position. The injector is disposed within the interior of the bottle when the injector is in the second position such that the predetermined amount of the gaseous sterilant is conveyed into the interior of the bottle.

In accordance with another embodiment of the present invention, there is provided a system for decontaminating bottles and the like as part of a continuous bottle-filling system. The system includes a rotary table for continuously moving bottles one after another along a first portion of a path. Each of the bottles has an interior. The rotary table includes a central hub, a first plate for supporting the bottles thereon and a second plate disposed above the first plate. The second plate has a plurality of receiving locations formed therein. Each of the plurality of receiving locations is dimensioned to receive one of the bottles. A sterilant feed conduit is connected at one end to a source of gaseous sterilant of a known concentration. An assembly is provided for distributing a predetermined amount of the gaseous sterilant from the source of gaseous sterilant to each of the bottles when the bottles are disposed along the first portion of the path. The assembly includes a plurality of injectors that are movable with the bottles. One of the plurality of injectors is associated with each of the bottles as the bottle moves along the first portion of the path. The injector is fluidly connected to the source of gaseous sterilant when the bottle associated with the injector is disposed along the first portion of the path such that the predetermined amount of the gaseous sterilant is conveyed around the bottle and into the interior of the bottle. The injector is movable between a first position and a second position relative to the bottle as the bottle moves along the path. The injector is disposed above the bottle when the injector is in the first position. The injector is disposed within the interior of the bottle when the injector is in the second position such that the predetermined amount of the gaseous sterilant is conveyed into the interior of the bottle.

According to yet another embodiment of the present invention, there is provided a method for decontaminating bottles and the like as part of a continuous bottle-filling system. The method includes the steps of:

a) moving bottles continuously along a path, each of the bottles having an interior;

b) providing a source of gaseous sterilant of a known concentration;

c) providing an assembly for distributing a predetermined amount of the gaseous sterilant from the source of gaseous sterilant to each of the bottles when the bottle is disposed along a first portion of the path, the assembly including a plurality of injectors movable with the bottles wherein one of the plurality of injectors is associated with each of the bottles as the bottle moves along the first portion of the path, the injector being fluidly connectable to the source of gaseous sterilant when the bottle is disposed along the first portion of the path;

d) moving the injector into a first position wherein the injector is disposed above the bottle;

e) conveying the predetermined amount of the gaseous sterilant through the injector wherein the gaseous sterilant fills the interior of the bottle and the gaseous sterilant is conveyed along an outer surface of the bottle; and f) moving the injector into a second position wherein the injector is disposed within the interior of the bottle such that the gaseous sterilant is introduced into the interior of the bottle.

An advantage of the present invention is a high-capacity decontamination system for decontaminating bottles and the like.

Another advantage of the present invention as described above is a decontamination system that utilizes vaporized hydrogen peroxide (VHP).

Another advantage of the present invention as described above is a decontamination system capable of producing large quantities of vaporized hydrogen peroxide from a single source.

Another advantage of the present invention is a decontamination system as described above having several methods for determining the concentration and flow of vaporized hydrogen peroxide through the system.

Another advantage of the present invention is a decontamination system as described above that is capable of modifying the flow of carrier gas therethrough.

Another advantage of the present invention is a decontamination system as described above that is capable of modifying the injection rate of liquid sterilant into the system.

Another advantage of the present invention is a decontamination system as described above that is capable of modifying the temperature of a carrier gas flowing therethrough.

Another advantage of the present invention is a decontamination system as described above that operates to maintain the concentration of vaporized hydrogen peroxide in a carrier gas at a level wherein the vaporized hydrogen peroxide has a dew point below the initial temperature of articles to be decontaminated.

A still further advantage of the present invention is a decontamination system as described above wherein system components are arranged such that un-vaporized hydrogen peroxide (if present) will flow downward through a system to be collected at a low point in the system.

Another advantage of the present invention is a decontamination system as described above having a sterilant supply system with a settling tank to eliminate entrained or trapped gas in a sterilant supply line to a vaporizer.

Another advantage of the present invention is a decontamination system as described above having an air process unit for filtering and drying air used within the system.

Another advantage of the present invention is a method of operating a system as described above to prevent condensation on articles or surfaces to be decontaminated.

Another advantage of the present invention is a method of operating a system as described above to maintain a desired concentration of vaporized hydrogen peroxide at the location where articles or surfaces are to be decontaminated.

Another advantage of the present invention is a method of operating a system as described above to maintain a fixed injection rate of liquid sterilant.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
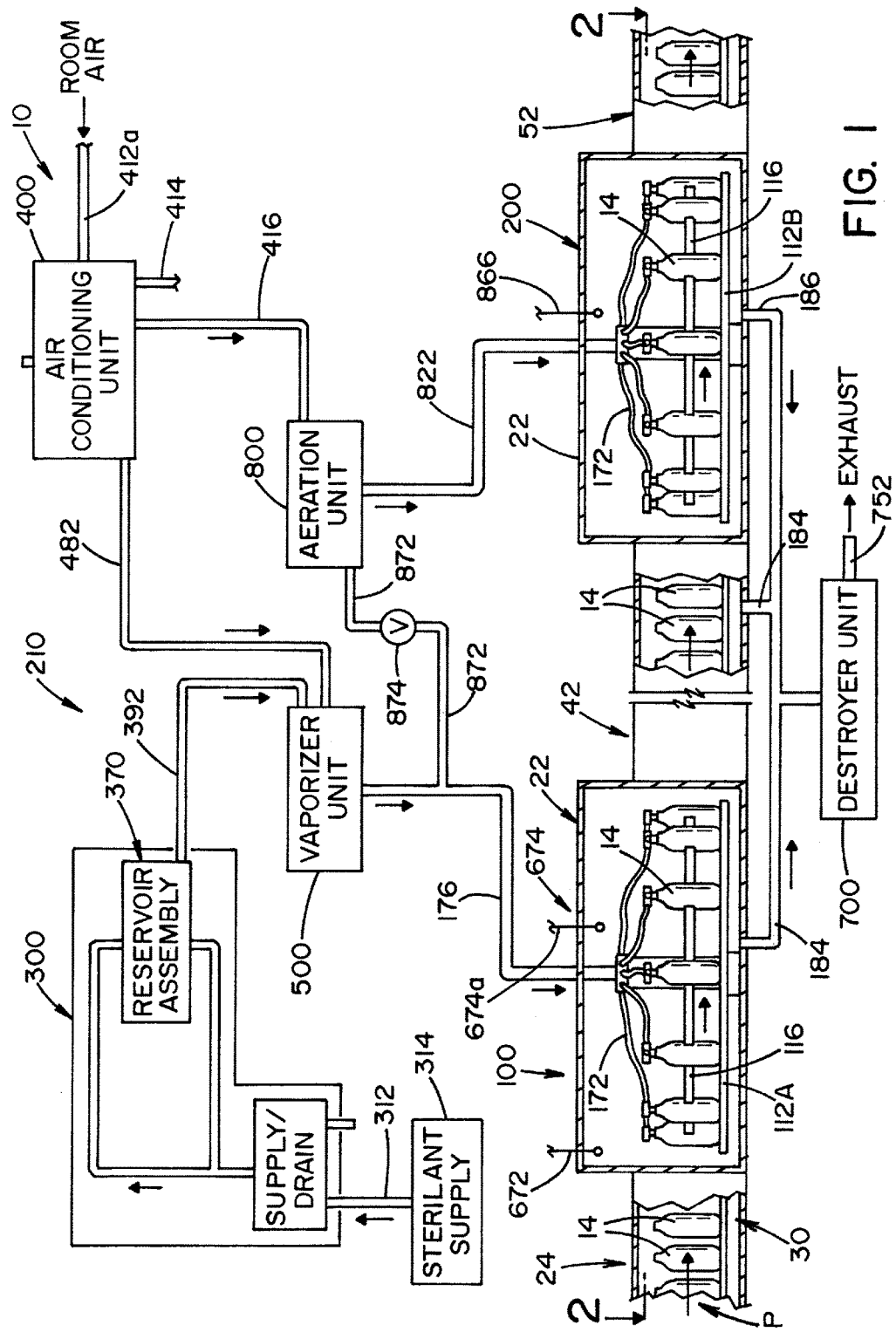
FIG. 1 is a drawing schematically illustrating a vaporized hydrogen peroxide decontamination system for decontaminating bottles and the like, illustrating a preferred embodiment of the present invention.
Figure 2:
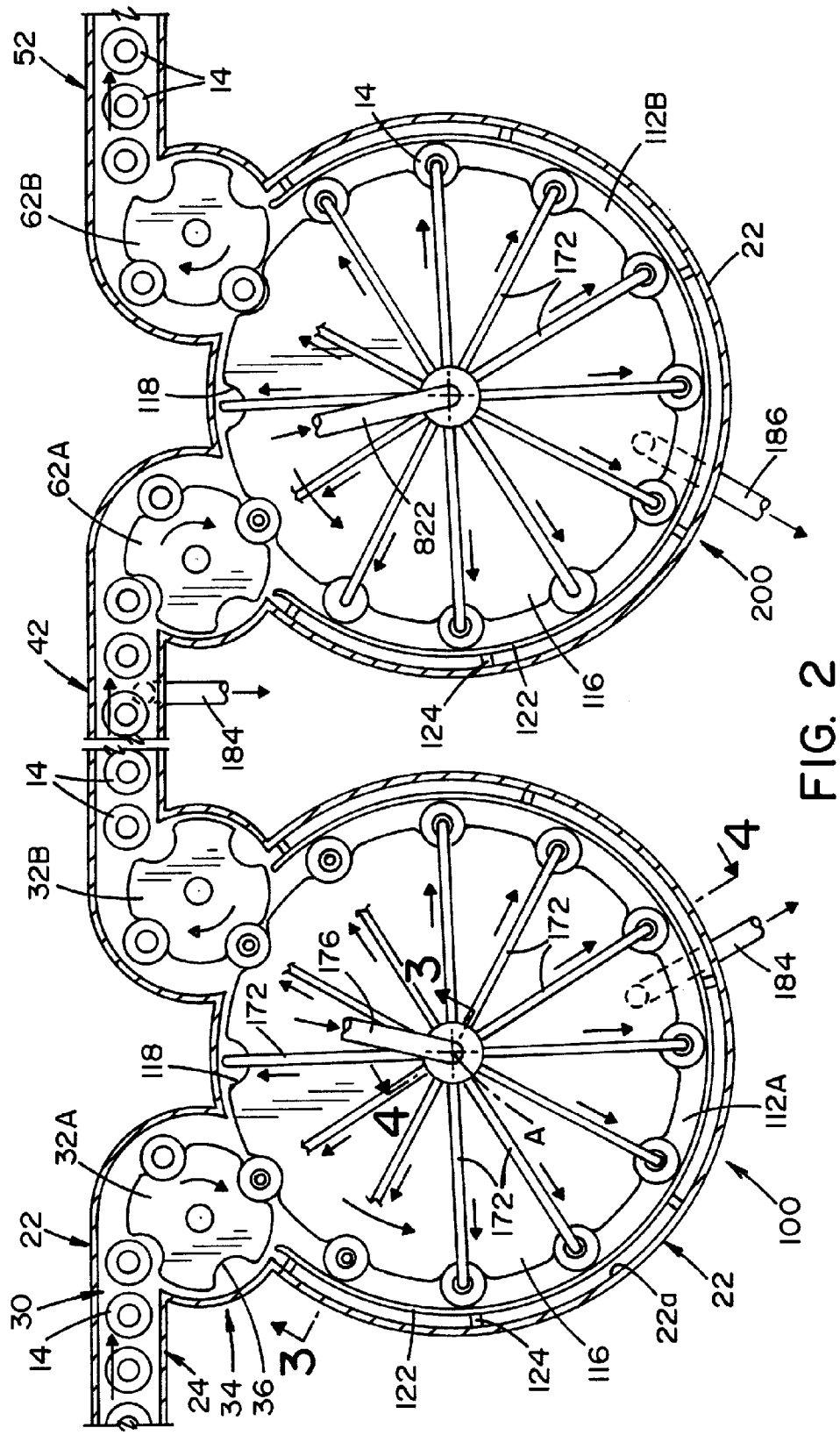
FIG. 2 is a sectional view taken along lines 2-2 of FIG. 1.

Referring now to the drawings wherein the showings are for the purpose of illustrating a preferred embodiment of the invention only, and not for the purpose of limiting same, FIG. 1 schematically illustrates a sterilization system for a continuous bottle-filling operation. More specifically, FIG. 1 shows a vaporized hydrogen peroxide decontamination system 10 for decontaminating bottles 14 continuously moving along path P. A cross-sectional plan view of a decontamination chamber 100 and an aeration chamber 200 are shown in FIG. 2. Bottles 14 to be decontaminated are conveyed along predetermined path P through decontamination chamber 100 and aeration chamber 200.

As illustrated in FIG. 2, a generally continuous housing 22 encloses bottle-conveying system 30 and decontamination chamber 100 and aeration chamber 200. In the embodiment shown, decontamination chamber 100 and aeration chamber 200 each house a rotary table 112 that conveys bottles 14 along a circular path through decontamination chamber 100 and aeration chamber 200, respectively.

Bottles 14 to be decontaminated are conveyed to decontamination chamber 100 along an enclosed entrance passageway 24. A first inlet rotary transfer device 32A at an inlet 34 to decontamination chamber 100 transfers bottles 14 from passageway 24 onto a rotary conveyor table 112A (which shall be described in greater detail below).

Bottles 14 travel along a circular path within decontamination chamber 100 and then exit decontamination chamber 100. Bottles 14 exiting decontamination chamber 100 are conveyed to aeration chamber 200 through an enclosed connecting passageway 42. A first outlet rotary transfer device 32B passes the spaced-apart bottles 14 from rotary table 112A in decontamination chamber 100 to the enclosed connecting passageway 42 that connects decontamination chamber 100 to aeration chamber 200. A second inlet rotary transfer device 62A passes bottles 14 from connecting passageway 42 to a rotary table 112B that is disposed within aeration chamber 200.

In aeration chamber 200, bottles 14 are conveyed along a circular path while clean, filtered air is blown into and around bottles 14 to remove residual VHP therefrom, as shall be described in greater detail below. Bottles 14 exiting aeration chamber 200 are transferred to an exit passageway 52 by a second outlet rotary transfer device 62B. As illustrated in FIG. 2, housing 22 defines decontamination chamber 100, aeration chamber 200, entrance passageway 24, connecting passageway 42 and exit passageway 52. Drive means (not shown) are provided to cause turntables 112A, 112B within decontamination chamber 100 and aeration chamber 200 respectively, and rotary transfer devices 32A, 32B, 62A, 62B to operate simultaneously to allow a continuous stream of bottles 14 to flow along path P through decontamination chamber 100 and aeration chamber 200.

Figure 3:
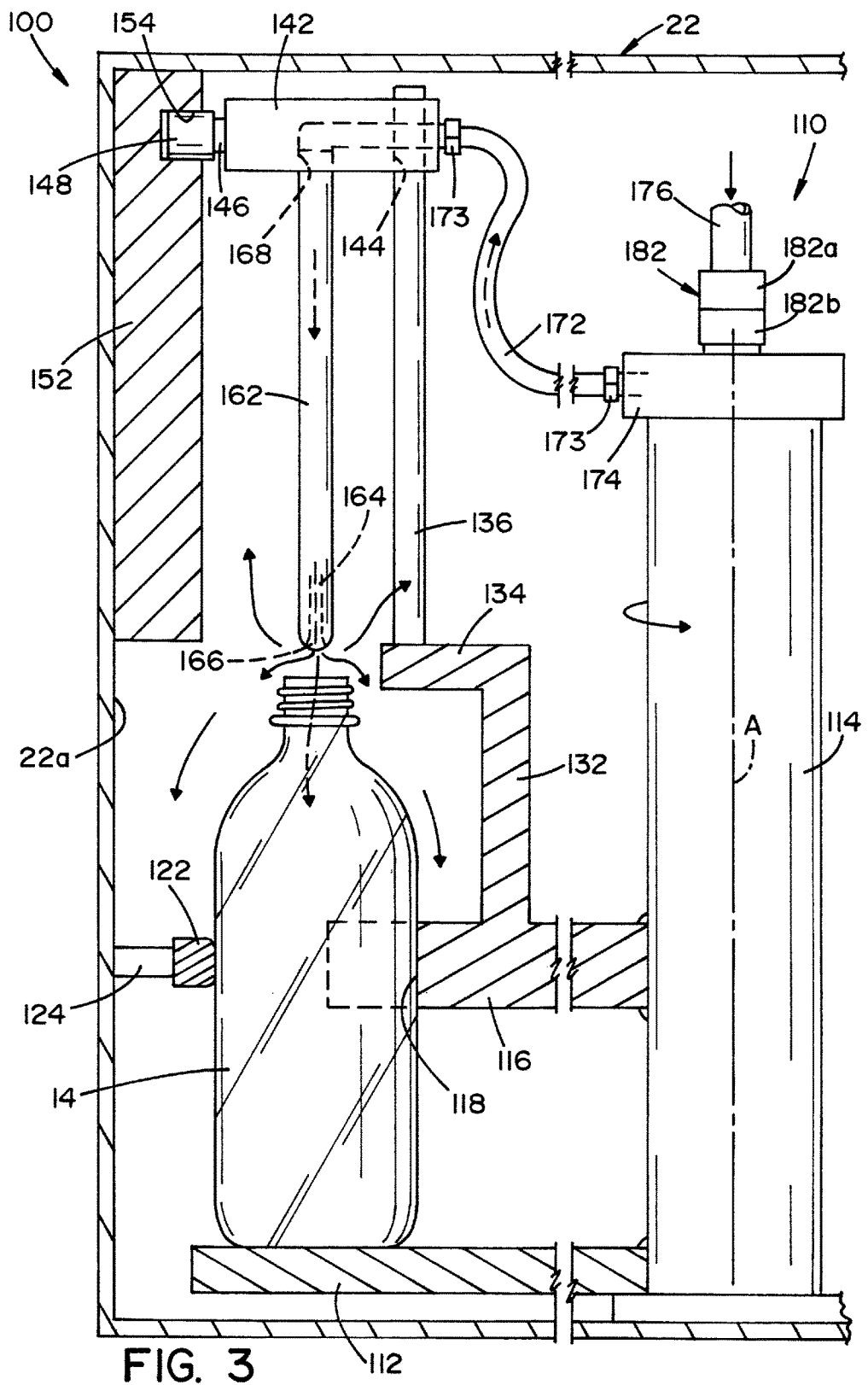
FIG. 3 is a sectional view taken along lines 3-3 of FIG. 2.
Figure 4:
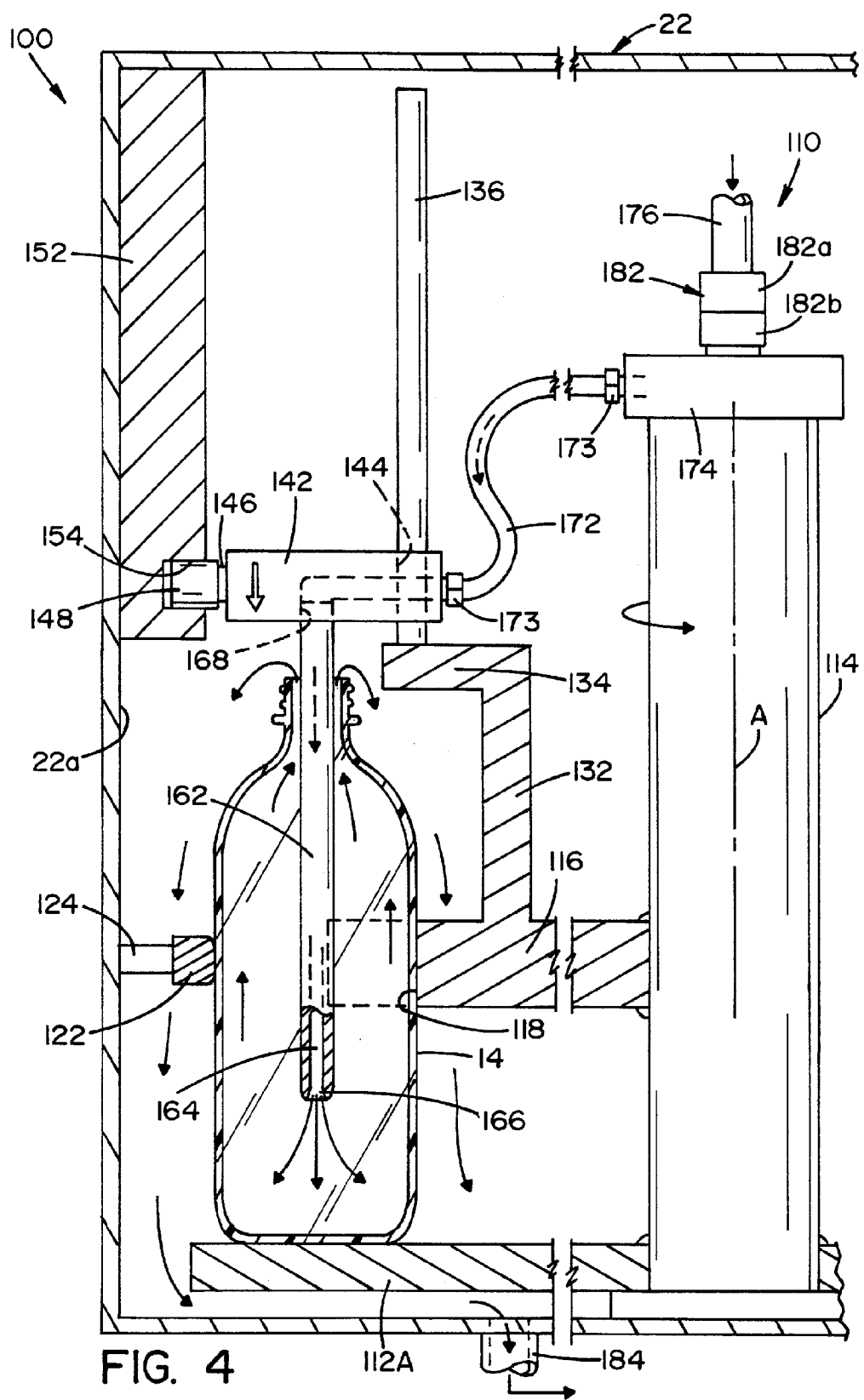
FIG. 4 is a sectional view taken along lines 4-4 of FIG. 2.

Referring now to FIGS. 3 and 4, an assembly 110 for decontaminating and aerating the interior of a bottle 14 as it moves along path P through decontamination chamber 100 is best seen.

A turntable 112 supports each bottle 14, as illustrated in FIGS. 3 and 4. Turntable 112 is a generally circular plate that is attached to a central hub or column 114. Central hub 114 is rotatable about a vertical axis, designated "A" in FIGS. 3 and 4. A second circular plate 116 is spaced above turntable 112. Plate 116 is secured to central hub 114 and has a plurality of equally-spaced-apart recesses 118 disposed along the peripheral edge thereof. Plate 116 is attached to hub 114 and is spaced a predetermined distance above turntable 112, as illustrated in FIGS. 3 and 4. Recesses 118 are semi-cylindrical in shape and are dimensioned to match the outer diameter of a bottle 14 to be decontaminated. In this respect, recesses 118 define a bottle-receiving cavity, as illustrated in the drawings. A rail 122 extending from an inner surface 22a of the chamber housing 22 is provided opposite to the outer peripheral edge of circular plate 116. Rail 122 is mounted on brackets 124 that extend from an inner surface of housing 22. Rail 122 is disposed to be uniformly spaced from the edge of plate 116 and recesses 118 defined therein. As illustrated in FIGS. 3 and 4, rail 122 is provided as a guide to confine a bottle 14 in the space between recess 118 and rail 122. In this respect, rail 122 provides a guide to a bottle 14 as the bottle 14 moves along circular path P through a decontamination chamber 100.

An annular wall 132 surrounds central hub 114. Annular wall 132 extends upwardly from the upper surface of plate 116. Wall 132 includes an outwardly extending flange 134 that supports a plurality of spaced-apart, vertically-oriented guide rods 136. In the embodiment shown, guide rods 136 are elongated, cylindrical shapes.

A guide rod 136 is associated with each recess 118 that is formed in circular plate 116. A slide 142 is provided to reciprocally move along each guide rod 136. Slide 142 is generally rectangular in shape, and includes a circular bore 144 through one end thereof. Bore 144 is dimensioned to receive guide rod 136 therethrough. A pin 146 extends from the opposite end of slide 142. A roller 148 is mounted on pin 146.

A guide plate 152 is mounted to inner surface 22a of housing 22. Guide plate 152 has a generally continuous guide slot 154 formed therein. Guide slot 154 extends about the inner periphery of decontamination chamber 100. Roller 148 on slide 142 is dimensioned to be received within guide slot 154 when slide 142 is mounted on guide rod 136. As will be described in greater detail below, roller 148 is movable through guide slot 154 to cause slide 142 to reciprocally move along guide rod 136.

Attached to slide 142 is an injector 162. In the embodiment shown, injector 162 is in the form of an elongated tube. Injector 162 has an inner passageway 164 extending axially therethrough. An orifice 166 is formed at the lower end of injector 162. The upper end of the injector 162 is received within an opening 168 in slide 142. In the embodiment shown, opening 168 is generally L-shaped and extends from the underside of slide 142 to the end of slide 142 that faces axis "A." Opening 168 communicates with passageway 164 through injector tube 162.

A connector hose 172 connects each slide 142 to a distribution block 174 on central hub 114. Fittings 173 at each end of connector hose 172 attach connector hose 172 to slide block 142 and distribution block 174. Distribution block 174 is connected to a high-capacity VHP vaporizer unit 500, best seen schematically in FIG. 1, and in more detail in FIGS. 5-10.

High-capacity vaporizer unit 500 is connected to distribution block 174 by a vaporized hydrogen peroxide feed line 176 and a rotary union 182. Rotary union 182 has an upper section 182a and a lower section 182b. Upper section 182a of rotary union 182 is stationary and lower section 182b of rotary union 182 is movable with distribution block 174 relative to upper section 182a. Upper section 182a and lower section 182b include opposing, mutually flat surfaces that abut and form a seal therebetween.

Vaporized hydrogen peroxide (VHP) is fed through feed line 176 to rotary union 182, and from rotary union 182 through distribution block 174 to connector hoses 172, and then to injectors 162, as illustrated by the arrows in FIGS. 2 and 3.

One or more VHP outlet lines 184 (best seen in FIG. 2) communicate with decontamination chamber 100 to convey VHP from decontamination chamber 100 to a VHP destroyer unit 700, as shall be described in greater detail below.

Referring now to aeration chamber 200, in the embodiment shown, aeration chamber 200 and turntable assembly 112 therein are the same as turntable assembly 112 in decontamination chamber 100. A major difference is that instead of a vaporizing sterilant being conveyed to injectors 162, as in decontamination chamber 100, in aeration chamber 200, dried, filtered air from an air conditioning unit 400 is conveyed through an aeration conduit 822 to a distribution block 174. Distribution block 174 directs the dried, filtered air to injectors 162 for purging residual VHP from the interior and exterior of bottles 14.

A flow of air is created through aeration chamber 200 by withdrawing air from aeration chamber 200 through one or more air outlet lines 186 (best seen in FIG. 2). Referring to FIGS. 1 and 5-10, a system 210 for generating VHP for decontamination chamber 100 is schematically illustrated.

Decontamination system 210, according to the present invention, is comprised of a sterilant supply unit 300, an air conditioning unit 400, a vaporizer unit 500, and a destroyer unit 700.

Sterilant Supply Unit 300

Figure 5:
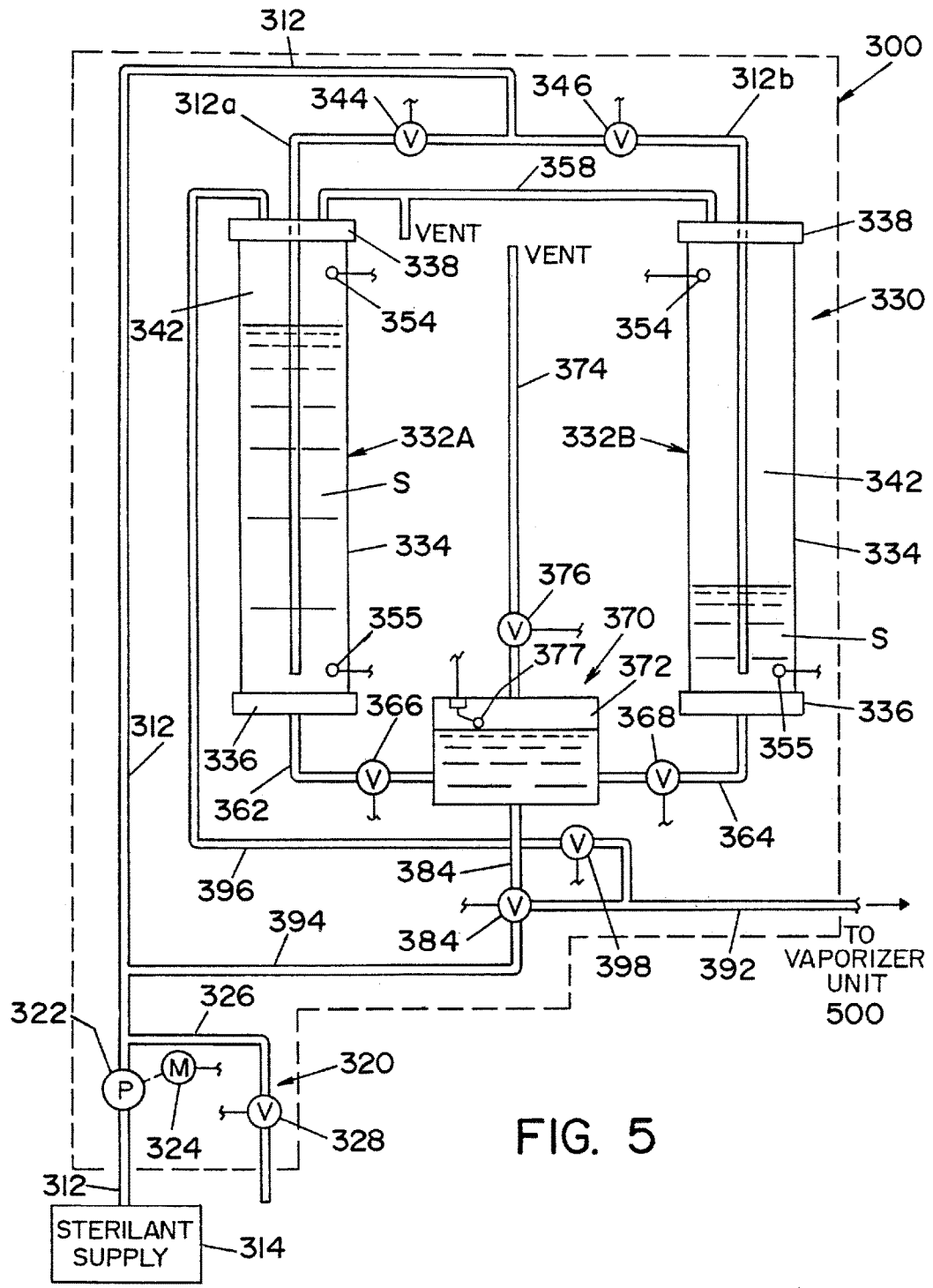
FIG. 5 is a drawing schematically illustrating a sterilant supply unit from the decontamination system shown in FIG. 1.

Referring now to FIG. 5, sterilant supply unit 300 is best seen. A supply line 312 connects sterilant supply unit 300 to an external supply 314 of liquid sterilant. A pump and drain assembly 320 is connected to supply line 312. Pump and drain assembly 320 includes a pump 322 driven by a motor 324. Pump 322 and motor 324 are designed to convey metered amounts of liquid sterilant to a reservoir assembly 330.

Reservoir assembly 330 preferably includes two reservoir tanks 332A, 332B. Two sterilant holding tanks 332A, 332B are provided to allow continuous, uninterrupted flow of sterilant to vaporizer unit 500. In this respect, one holding tank 332A may be filled with sterilant, while the other tank 332B is being used to provide sterilant to vaporizer unit 500, as shall be described in greater detail below. Tanks 332A, 332B are essentially identical, and therefore, only tank 332A shall be described in detail, it being understood that the description of tank 332A applies to tank 332B.

Tank 332A is generally columnar in shape, and is comprised of a tubular shell or wall 334 having a base 336 and a cover 338 at the ends thereof. In a preferred embodiment, tubular shell 334 is cylindrical in shape and is formed of a translucent material. Tank 332A defines an inner chamber 342 for holding a liquid sterilant S. Supply line 312 is connected to reservoir tanks 332A, 332B by branch supply lines 312a, 312b. Valves 344, 346 are disposed respectively in branch supply lines 312a, 312b to control flow of liquid sterilant S to reservoir tanks 332A, 332B. Each tank 332A, 332B includes level sensor 354. Sensor 354 is provided to indicate an "overfill level," as shall be described in greater detail below. A pressure sensor 355 is provided at the bottom of each tank 332A, 332B to provide pressure signals that are indicative of the level of fluid in each tank 332A, 332B.

Tanks 332A, 332B are connected at their bottom ends to a holding tank 370 by fluid conduits 362, 364, respectively. Control valves 366, 368 are disposed respectively in fluid conduits 362, 364 to control the flow of sterilant from reservoir tanks 332A, 332B to holding tank 370. The upper ends of reservoir tanks 332A, 332B are connected to a vent line 358, as schematically illustrated in FIG. 5.

Holding tank 370 defines air enclosed in holding chamber 372. A vent line 374 extends upwardly from holding chamber 372. A control valve 376 is disposed within vent line 374 to control flow therethrough. As best seen in FIG. 5, vent line 374 has a length such that the upper end of vent line 374 is disposed at the upper ends of reservoir tanks 332A, 332B. A level sensor 377 is disposed within holding chamber 372 of holding tank 370 at a predetermined level. A level sensor 377 is disposed within holding tank 370. In the embodiment shown, level sensor 377 is a float switch.

A fluid conduit 384 extending from the bottom of holding tank 370 connects holding chamber 372 to a control valve 386 that regulates flow of sterilant from holding tank 370 to either a vaporizer feed line 392 or to a drain line 394 that is connected to supply line 312. As illustrated in FIG. 5, drain line 394 is in fluid communication with drain line 326 of pump and drain assembly 320. A return line 396 extends from vaporizer feed line 392 to the top of tank 332A. A control valve 398 is disposed within return line 396 to control the flow of sterilant therethrough.

Vaporizer feed line 392 is connected to vaporizer unit 500, as illustrated in the drawings. Sterilant from holding tank 370 is preferably fed by gravity to vaporizer unit 500. Accordingly, in the embodiment shown, holding tank 370 and reservoir tanks 332A, 332B are disposed above vaporizer unit 500, i.e., at a higher elevation.

Air Conditioning Unit 400

Figure 8:
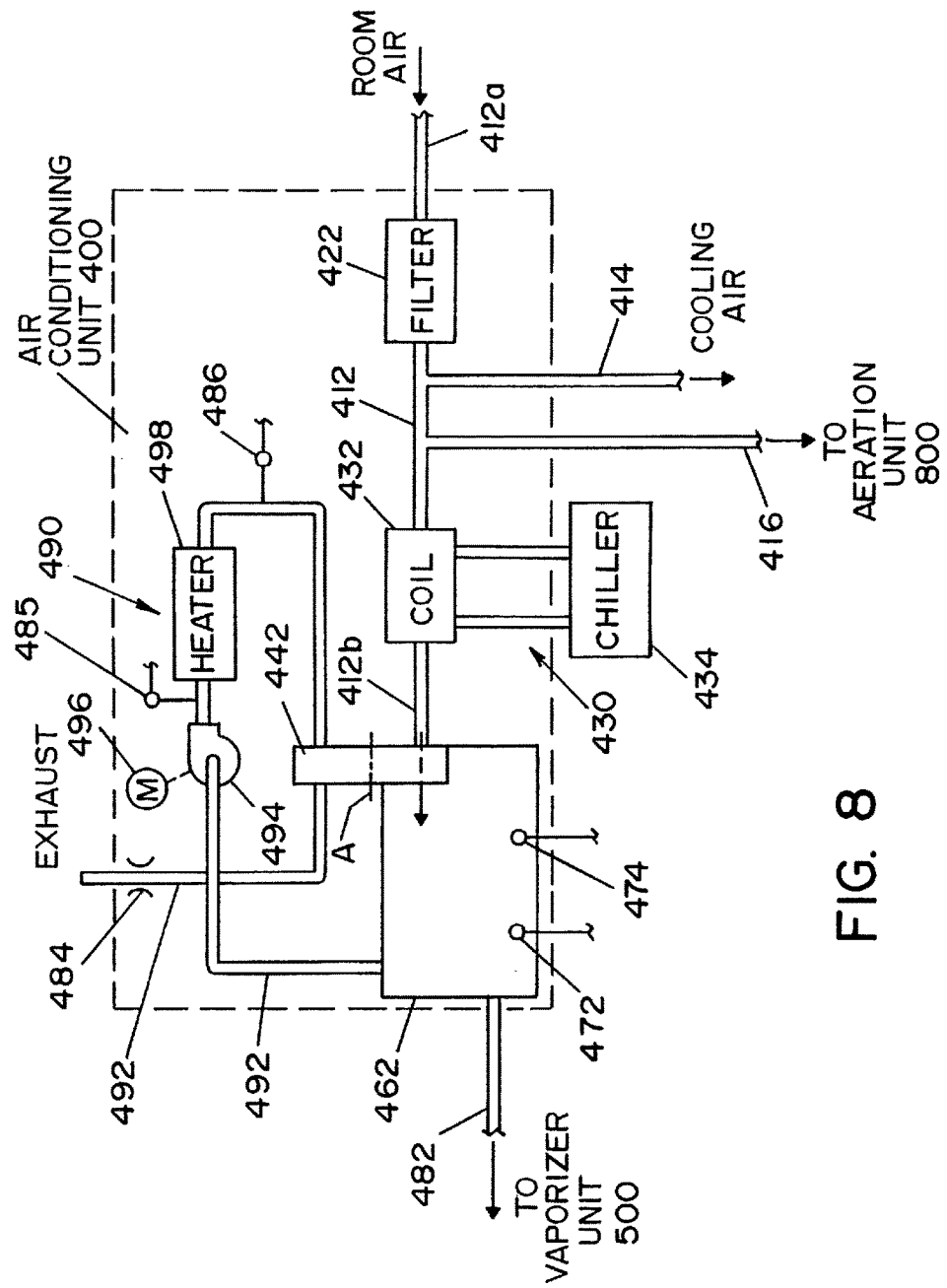
FIG. 8 is a drawing schematically illustrating an air conditioning unit from the decontamination system shown in FIG. 1.

Referring now to FIG. 8, the air conditioning unit 400 is best illustrated. Air conditioning unit 400 is provided to condition, i.e., to filter and to dry air used in vaporizer unit 500, and to filter air used by aeration unit 800. Air conditioning unit 400 is basically comprised of a filter 422, a cooling assembly 430 and a desiccant wheel 442 arranged in series.

An air inlet conduit 412 has a first end 412a that communicates with the environment, namely room air. Another end 412b of air inlet conduit 412 is connected to chamber 462 within air conditioning unit 400. Filter 422 is disposed within air inlet conduit 412 to filter air flowing therethrough. Filter 422 is preferably a HEPA filter. Cooling assembly 430 is disposed downstream from filter 422. Cooling assembly 430 is comprised of a cooling coil 432 and a chiller 434 that is connected to cooling coil 432. Cooling coil 432 surrounds air inlet conduit 412. Chiller 434 is dimensioned to provide sufficient cooling to coil 432 surrounding air inlet conduit 412 such that air flowing through air inlet conduit 412 is chilled to precipitate moisture within the air. In other words, chiller 434 has sufficient capacity to dehumidify air flowing through air inlet conduit 412. Between filter 422 and cooling coil 432, an air supply line 414 is connected to air inlet conduit 412. Air supply line 414 provides filtered air throughout system 10 to cool electronics (not shown). A second air supply line 416 is connected to air inlet conduit 412 between filter 422 and cooling coil 432. Second air supply line 416 provides filtered air to aeration unit 800, as shall be described in greater detail below. Desiccant wheel 442, rotatable about a first axis "A," is disposed at end 412b of air inlet conduit 412, i.e., downstream from filter 422 and cooling coil 432. Desiccant wheel 442 is disposed such that half of wheel 442 rotates into chamber 462. End 412b of air inlet conduit 412 directs air flow through that portion of desiccant wheel 442 that is positioned within chamber 462. Desiccant material within desiccant wheel 442 is operable to absorb moisture in the air flowing through air inlet conduit 412. Thus, air entering chamber 462 has been filtered and dried by means of filter 422, cooling coil 432 and desiccant wheel 442. A humidity sensor 472 and a temperature sensor 474 are disposed within chamber 462 to monitor respectively the humidity and temperature of the air within chamber 462. Chamber 462 is in fluid communication with vaporizer units 500 via air line 482, as illustrated in FIG. 5.

Air conditioning unit 400 includes a regeneration system 490 for regenerating, i.e., removing moisture from, desiccant wheel 442. A regeneration conduit 492 is connected to chamber 462. A blower 494, driven by a motor 496, draws dried and filtered air within chamber 462 and directs the dried air through a heater 498 that heats the dry air. Regeneration conduit 492 is arranged to direct the heated, dried, filtered air through that portion of desiccant wheel 442 that is outside of chamber 462. As will be appreciated by those skilled in the art, the heated air dries, i.e., removes moisture from desiccant wheel 442. Moist air flowing from desiccant wheel 442 through regeneration conduit 492 flows out of air conditioning unit 400 through an orifice 484. A pressure transducer 485 is disposed at the outlet, i.e., downstream, of blower 494. Pressure transducer 485, in conjunction with orifice 484, is used to establish a desired air flow through conduit 492, to ensure proper moisture removal. A temperature sensor 486 monitors the temperature of the air exiting heater 498. The temperature in conduit 492 is controlled to ensure proper moisture removal.

Vaporizer Unit 500

Figure 6:
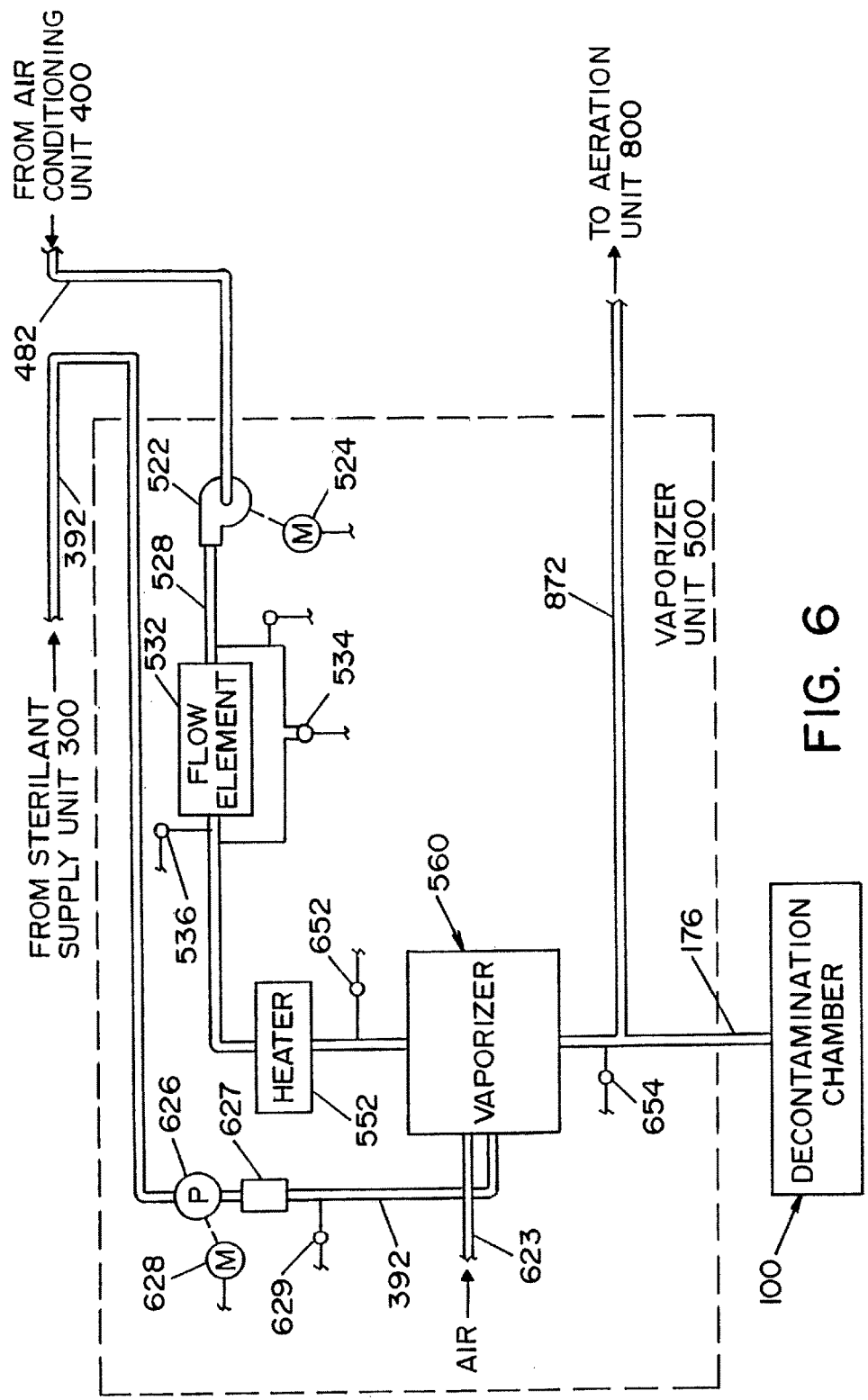
FIG. 6 is a drawing pictorially illustrating a vaporizer unit from the decontamination system shown in FIG. 1.
Figure 10:
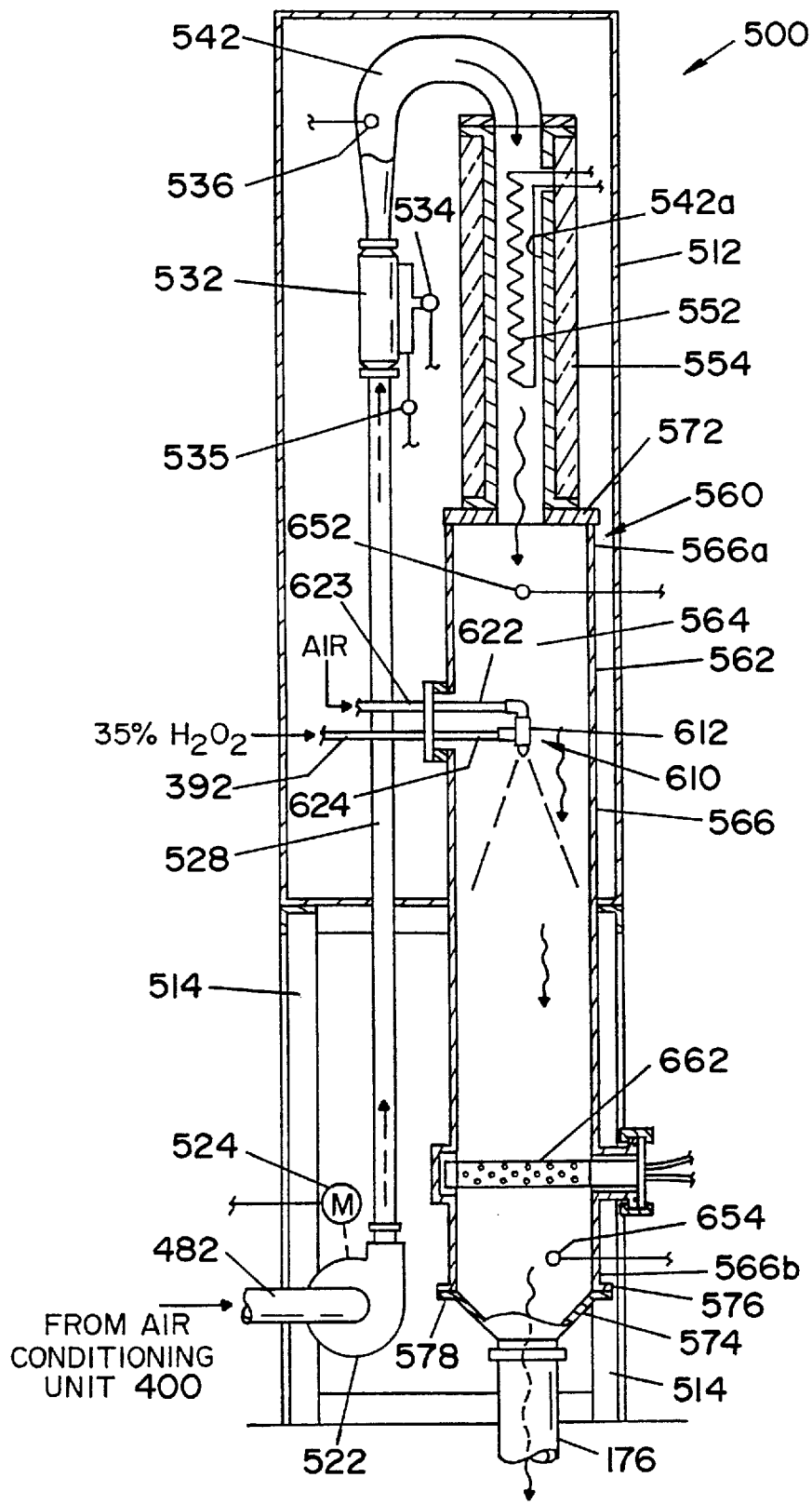
FIG. 10 is a sectional view of a vaporizer from the decontamination system shown in FIG. 1.

Referring now to FIGS. 6 and 10, vaporizer unit 500 is best seen. Vaporizer unit 500 is connected to vaporizer feed line 392 from sterilant supply unit 300, and is connected to air line 482 from air conditioning unit 400.

Vaporizer unit 500 is comprised of a blower 522, a flow element 532 for measuring airflow, a heater 552 and a vaporizer 560, that are all schematically illustrated in FIG. 6, and pictorially illustrated in FIG. 10.

In the embodiment shown, vaporizer unit 500 includes a cabinet or housing 512 mounted on a structural steel support frame 514. Cabinet 512 and support frame 514 together define an upright, columnar structure. A blower 522 is disposed at a bottom location of support frame 514. Blower 522 is driven by a motor 524. Motor 524 is preferably a variable speed motor, wherein the output of blower 522 can be controlled to increase air flow therethrough. The inlet of blower 522 is connected to air line 482 from air conditioning unit 400. When in operation, blower 522 draws air through air conditioning unit 400 where the air is then dried and filtered. In the embodiment shown, the outlet of blower 522 is connected to a vertical conduit 528. A flow element 532 is disposed within conduit 528 to measure air flow through conduit 528. Flow element 532 is preferably a Venturi device. A sensor 534 measures a pressure difference across the Venturi device and provides a signal indicative of the air flow through flow element 532. A Venturi device is preferable because of the high resolution of air flow it can provide and because of the low loss of power for the air flowing therethrough. A pressure sensor 535 is provided to measure the static pressure to flow element 532, to facilitate calculation of the mass air flow rate through conduit 528, as shall be described in greater detail below. A temperature sensor 536 is disposed downstream from flow element 532.

In the embodiment shown, a generally U-shaped conduit section 542 is connected to flow element 532 to redirect the flow of air. Conduit section 542 includes an elongated straight heater section 542*a* that is vertically oriented in the embodiment shown. As illustrated in FIG. 10, the passageway defined by conduit section 542 increases in a cross-sectional area from the end of conduit section 542 that connects to flow meter 532 to elongated straight heater section 542*a*. A heating element 552 is positioned within straight heater section 542*a* of conduit section 542 and is provided to heat the air flowing through conduit section 542. In the embodiment shown, heating element 552 is an electrical device. An insulating layer 554 surrounds and encloses heating element 552. Heating element 552 is designed to be capable of heating air flowing through conduit section 542 up to a temperature high enough to vaporize hydrogen peroxide and high enough to maintain a desired temperature sufficient to prevent condensation in system 10. In one embodiment, heating element 552 is capable of heating air flowing through conduit section 542 to at least about 105° C. In another embodiment, heating element 552 is capable of heating air flowing through conduit section 542 to at least 180° C. The increase in the cross-sectional area of conduit section 542 allows the smaller piping from flow element 532 to connect to the larger diameter of heater section 542*a*.

A vaporizer 560 is connected to the end of conduit section 542 downstream from heater 552. Vaporizer 560 is comprised of a housing 562 defining an elongated inner vaporizing plenum 564. In the embodiment shown, housing 562 is comprised of a rectangular shell 566 having a first end 566*a* having a flat cap 572 thereon, and a second end 566*b* having a funnel-shaped base 574. The cross-sectional area and the length of housing 562 are dimensioned to allow sufficient time for the liquid sterilant to be vaporized therein. First end 566*a* of vaporizer 560 defines an inlet end, and second end 566*b* of vaporizer 560 defines an outlet end. Shell 566, cap 572 and base 574 are preferably formed of metal, and more preferably, of aluminum. Cap 572 is secured to shell 566, preferably by welding. Conduit section 542 communicates with inner plenum 564 of vaporizer 560 through an opening in cap 572. Outlet end 566*b* of shell 566 includes an annular flange 576 for connecting to an annular flange 578 on base 574. Base 574 is funnel-shaped and connects vaporizer housing 562 to a vaporized hydrogen peroxide feed line 174 that in turn is connected to decontamination chamber 100.

As illustrated in FIG. 10, vaporizer 560 is oriented such that the elongated vaporizer plenum 564 is vertically oriented. In this respect, heating element 552 and straight section 542*a* of conduit section 542 are vertically aligned with vaporizer plenum 564 so as to direct heated air downwardly through vaporizer plenum 564.

A sterilant injection system 610 is disposed within vaporizer plenum 564. Injection system 610 is centrally disposed within plenum 564, and is oriented to inject sterilant into plenum 564 in a downwardly direction toward second end 566*b* of vaporizer housing 562.

Injection system 610 is comprised of a tubular body 612 that defines an inner mixing chamber 614. An air line 622 and a sterilant line 624 connect to body 612 and communicate with inner mixing chamber 614. Air line 622 is connected to a source (not shown) of filtered, dry pressurized air within system 10 by conduit 623. Sterilant line 624 is connected to sterilant supply line 392 from sterilant supply unit 300. A pump 626, driven by a motor 628, schematically illustrated in FIG. 6, is disposed in sterilant supply line 392 to feed sterilant under pressure into injection system 610. Pump 626 is preferably a variable-speed peristaltic pump. Pump 626 is provided to pump sterilant into injection system 610 at a selected rate. (The injection rate in grams per minute is measured by a mass meter 627.) Motor 628 is preferably a variable speed motor wherein the injection rate of sterilant to injection system 610 can be varied by the speed of motor 628. A pressure sensor 629 is disposed in sterilant supply line 392, downstream from pump 626. Pressure sensor 629 monitors (and ensures) proper sterilant injection rate and ensures that the injection system 610 does not become obstructed.

Figure 10A:
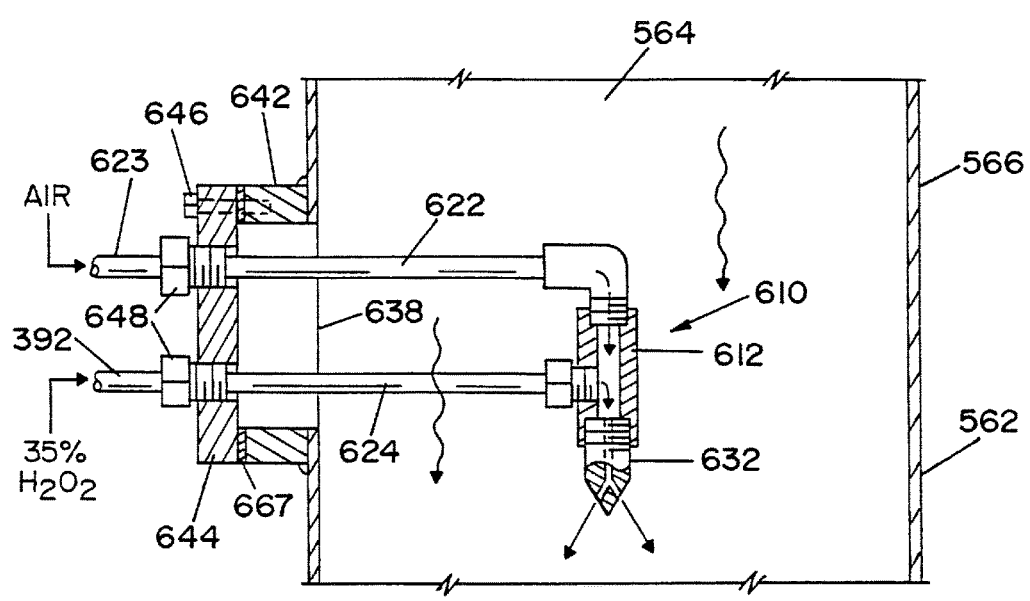
FIG. 10A is an enlarged view of an atomizer from the vaporizer unit shown in FIG. 10.

Referring now to FIG. 10A, an atomizing nozzle 632 is, attached to body 612. Nozzle 632 is preferably capable of creating a fine spray of sterilant, i.e., namely a mist that is sufficiently small to ensure complete vaporization. A commonly available atomizing nozzle finds advantageous application in the present invention.

To facilitate positioning injection system 610 within vaporizer plenum 564, an opening 638 is formed in the side of shell 566. A collar 642 is attached, preferably by welding, to shell 566 to surround opening 638. A cover plate 644 is attached to collar 642 with conventional fasteners 646. A gasket 667 is disposed between cover plate 644 and collar 642 to provide a complete seal. Threaded openings in cover plate 644 receive conventional fittings 648 that connect air line 622 to an air conduit 623, and sterilant line 624 to sterilant supply line 392.

According to one aspect of the present invention, nozzle 632 is dimensioned relative to shell 566 such that contact of spray from nozzle 632 with shell 566 is minimized or avoided during operation of vaporizer 560.

A temperature sensor 652 is disposed within vaporizer plenum 564 between first end 566a of vaporizer 560 and sterilant injection system 610. A second temperature sensor 654 is disposed within vaporizer plenum 564 downstream from sterilant injection system 610 near second end 566b of vaporizer housing 562. The temperature drop between sensors 652, 654 is proportional to the heat necessary to vaporize the sterilant, as shall be discussed in greater detail below.

A vaporized hydrogen peroxide sensor 662, that is capable of providing an indication of the concentration of vaporized hydrogen peroxide and water vapor, is optionally disposed within vaporizer plenum 564 downstream from sterilant injection system 610. Vaporized hydrogen peroxide sensor 662 is disposed near second end 566b (the outlet end) of vaporizer 560. Sensor 662 is preferably an infrared (IR) sensor, and more preferably a near infrared (IR) sensor. Sensor 662 is generally cylindrical in shape, and is mounted in housing 562 to traverse plenum 564. Sensor 662 is mounted to housing 562 to be easily removable therefrom.

As illustrated in FIG. 1, vaporized hydrogen peroxide feed line 176 connects vaporizer unit 500 to decontamination chamber 100. As indicated above, decontamination chamber 100 is comprised of an enclosure or housing 22 that defines a space or region through which bottles 14 to be sterilized/decontaminated are conveyed.

As best seen in FIG. 1, a temperature sensor 672 and a vaporized hydrogen peroxide sensor 674 are disposed within housing 22. Vaporized hydrogen peroxide sensor 674 is capable of providing an indication of the concentration of vaporized hydrogen peroxide and water vapor. Sensor 674 is preferably a near infrared (IR) sensor. Sensor 674 is cylindrical in shape and has fiber optic cables 674a extending therefrom.

Destroyer Unit 700

Figure 9:
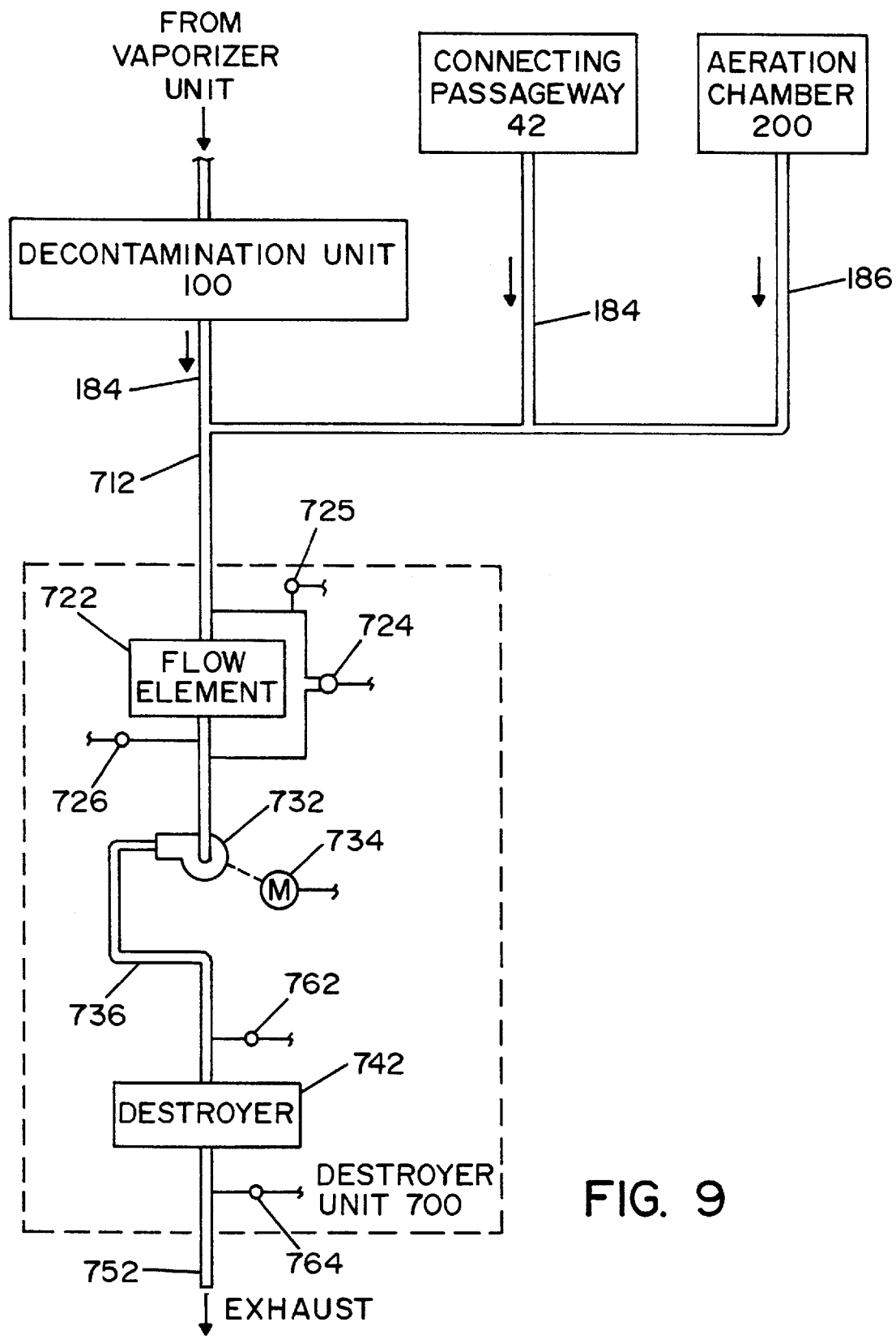
FIG. 9 is a drawing schematically illustrating a destroyer unit from the decontamination system shown in FIG. 1.

Referring now to FIG. 9, destroyer unit 700 is schematically illustrated.

VHP outlet lines 184 from decontamination chamber 100 and connecting passageway 42 and VHP outlet line 186 from aeration chamber 200 are connected to destroyer unit 700. A flow measuring device 722 is disposed within conduit 712 to provide data with respect to flow therethrough. In the embodiment shown, flow measuring device 722 includes a pressure sensor 724 that is operable to sense a pressure difference across flow measuring device 722 and to provide a signal indicative of flow through device 722. In a preferred embodiment, flow measuring device 722 is a Venturi device. An additional pressure sensor 725 is provided to measure static pressure in the flow measuring device 722, for mass flow calculations as shall be discussed below. A temperature sensor 726 is disposed within conduit 712 downstream from flow measuring device 722. Conduit 712 is connected to the inlet end of a blower 732 that is driven by a motor 734. A conduit 736 extending from the outlet side of blower 732 is connected to a destroyer 742. Destroyer 742 is basically a catalytic device that is operable to destroy hydrogen peroxide flowing therethrough. In this respect, catalytic destroyers convert the vaporized hydrogen peroxide into water and oxygen. A temperature sensor 762 is disposed in front, i.e., upstream, of destroyer 742. A second temperature sensor 764 is disposed behind, i.e., downstream, from destroyer 742.

Aeration Unit 800

Figure 7:
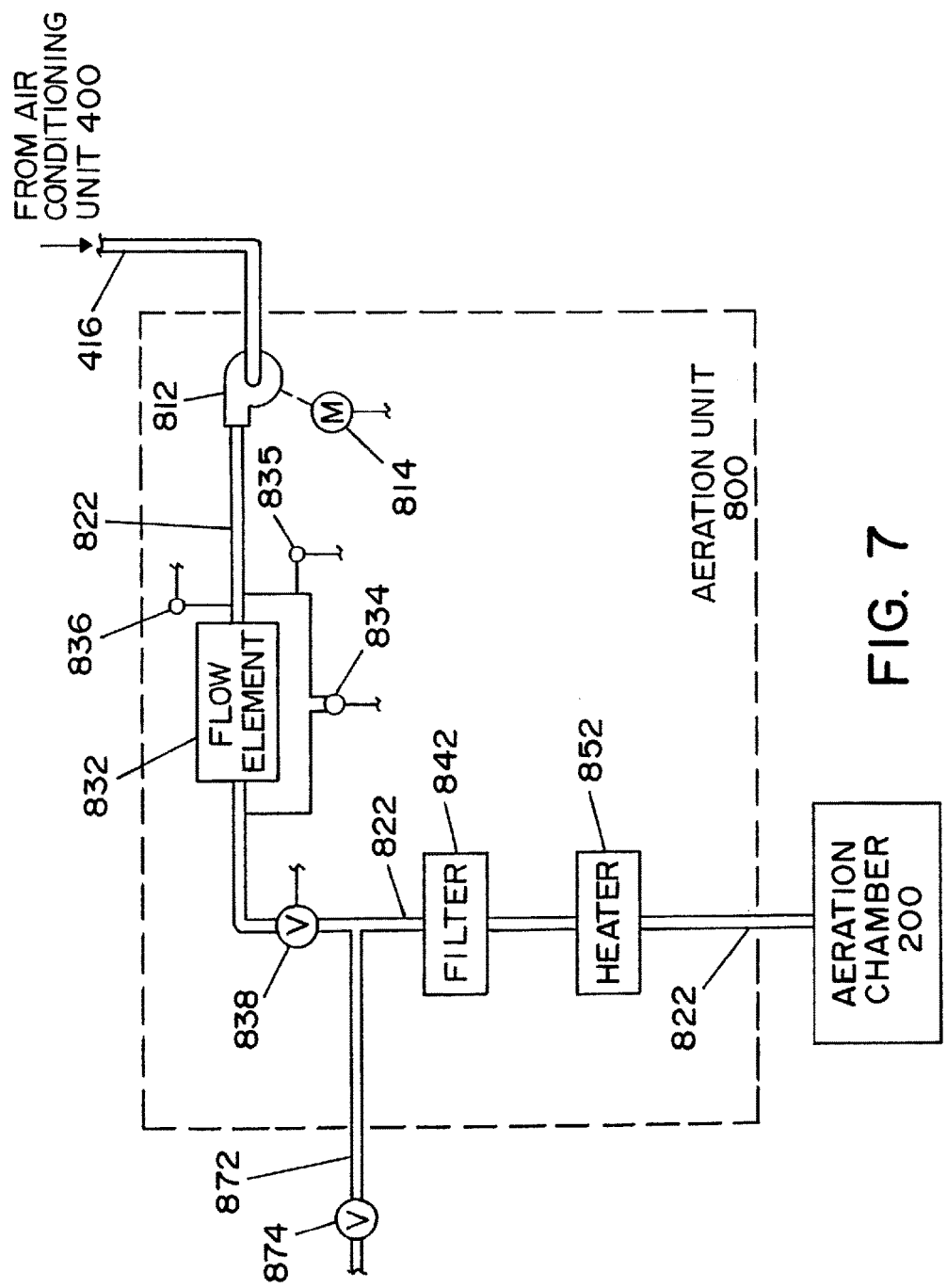
FIG. 7 is a drawing schematically illustrating an aeration unit from the decontamination system shown in FIG. 1.

Referring now to FIG. 7, aeration unit 800 is schematically illustrated. Aeration unit 800 is connected to air supply line 416 from air conditioning unit 400. Air supply line 416, from air conditioning unit 400, supplies filtered air to aeration unit 800. Air supply line 416 is connected to the inlet side of a blower 812 that is driven by a variable-speed motor 814. Blower 812 is disposed within aeration unit 800 to draw air through filter 422 in air conditioning unit 400 and through supply line 416. The outlet side of blower 812 is connected to an aeration conduit 822. Aeration conduit 822 extends through aeration unit 800. Downstream from blower 812, a flow measuring device 832 is disposed within aeration conduit 822. In a preferred embodiment, flow measuring device 832 is a Venturi device. A pressure sensor 834 measures the pressure difference across flow measuring device 832 that provides signals indicative of the flow through aeration conduit 822. A pressure sensor 835 is provided to measure the static pressure to flow measuring device 832, to facilitate calculation of the mass flow rate through aeration conduit 822. A temperature sensor 836 is disposed before (upstream of) flow measuring device 832. Temperature sensor 836 is disposed between blower 812 and flow measuring device 832. A valve element 838 is disposed in aeration conduit 822 downstream from flow measuring device 832 to regulate the amount of flow through aeration conduit 822. A filter element 842 is disposed downstream from valve element 838. Filter element 842, preferably a HEPA filter, provides a second filtration of the air flowing through aeration conduit 822, in addition to filter 422 in air conditioning unit 400. A heating element 852 is disposed in aeration conduit 822 downstream from filter element 842. As stated above aeration conduit 822 connects to distribution block 174 in aeration chamber 200. A temperature sensor 866 is disposed within aeration chamber 200.

Aeration unit 800 basically provides heated, filtered air to aeration chamber 200 to purge peroxide vapor from bottles 14 and to prevent condensation.

As best seen in FIG. 6, a conduit 872 connects vaporized hydrogen peroxide feed line 176 to aeration conduit 822. Conduit 872 is connected to vaporized hydrogen peroxide feed line 176 between vaporizer 560 and decontamination chamber 100. As best seen in FIG. 7, conduit 872 is connected to aeration conduit 822 between valve 838 and filter element 842. A valve 874 is disposed in conduit 872 to control flow therethrough. Conduit 872 is provided to periodically decontaminate filter element 842 in aeration unit 800. By closing valve 838 in aeration conduit 822 and by opening valve 874 in conduit 872, vaporized hydrogen peroxide can be directed from vaporizer 560 through filter element 842.

As provided in the present invention, by controlling the air temperature, air flow rate, sterilant temperature and sterilant injection rate in a decontamination system, a desired concentration of vaporized hydrogen peroxide can be maintained within a decontamination chamber. When using vaporized hydrogen peroxide (VHP) in a decontamination system, it is necessary to prevent the vaporized hydrogen peroxide from condensing on the products or articles to be decontaminated. In a steady state, steady flow vaporized hydrogen peroxide process, the sterilant injection rate, the air flow rate and the air temperature must be controlled to prevent condensation. According to the present invention, the hydrogen peroxide vaporizer system is controlled to a desired vaporized hydrogen peroxide concentration and temperature, to prevent condensation. According to one aspect of the present invention, the operation of system 10 is controlled to maintain the concentration of hydrogen peroxide in an air stream at a dew point temperature that is below the temperature of articles to be decontaminated. System 10 is controlled based upon a mathematical model that shall now be described.

It is known that the dew point concentration of a water and hydrogen peroxide sterilant is dependent on the temperature of the air—into which the sterilant is injected—and the concentration of the water and peroxide in the air. In the case of a steady state, steady flow process, as is used with vaporized hydrogen peroxide decontamination equipment, the dew point concentration is dependent on the injection rate of the sterilant and the temperature and the volumetric flow of air past the injector.

The concentration of hydrogen peroxide $C_p$ in the air stream (mg/liter) can be determined by the following equation:

$$C_p = \frac{I*1000}{F*28.32}\left(\frac{P}{100}\right)E \quad (1)$$

where:
I=sterilant injection rate (grams/min)
F=air flow rate (actual ft$^3$/min)
P=percent of peroxide in sterilant
E=vaporizer efficiency (0.90=90%) which is a function of the amount of hydrogen peroxide broken down in the vaporization process.

In the equation, the 1000 is a conversion factor for converting grams to milligrams. The 28.32 is a conversion factor for converting cubic feet to liters.

The concentration of water vapor $C_w$ in the air stream (mg/liter) can be determined by the following equation:

$$C_w = \frac{I*1000}{F*28.32}\left(\frac{100-P}{100}\right) + \frac{I*1000}{F*28.32}\left(\frac{P}{100}\right)(1-E)\frac{9}{17} + C_{w,air} \quad (2)$$

Hydrogen peroxide breaks down into water and oxygen. Nine-seventeenths of the catalyzed hydrogen peroxide is converted into water with the balance being converted to oxygen. This is seen in equation 2 which adds the water portion of the catalyzed hydrogen peroxide to the concentration of water seen in the air stream.

$C_{w,air}$=concentration of water in the air stream flowing into the vaporizer (mg/liter)

From equations (1) and (2), the concentration of water and hydrogen peroxide in the air stream can be determined. The dew point of the hydrogen peroxide is determined based on the following.

It is known that when liquid of a given concentration of $H_2O_2$ is placed in an enclosure with no initial humidity, the liquid hydrogen peroxide and water will evaporate and reach equilibrium in the enclosure. The concentration of the hydrogen peroxide vapor will be lower than hydrogen peroxide concentration found in the liquid. From known sources, such as a book entitled: "Hydrogen Peroxide" by Schumb, Satterfield, & Wentworth ©1955, equations and a table provide the relationship between the liquid and gas concentrations for $O_2O_2$ and water. Within an enclosure, the vapor concentration will reach the saturation point.

Source information is used to determine the saturation point of water and hydrogen peroxide mixtures in a given volume.

In this respect, the mole fraction of hydrogen peroxide in phase gas ($\gamma_h$) over a hydrogen peroxide-water solution (liquid form) is given by the following equation.

$$y_h = \frac{p_{hg}x_h\gamma_h}{P} = \frac{p_{hg}x_h\gamma_h}{(p_{wg}x_w\gamma_w)+(p_{hg}x_h\gamma_h)} \quad (3)$$

where:
$x_h$=Mole fraction of hydrogen peroxide in liquid sterilant
P=Total vapor pressure of the mix (mm Hg).
The total vapor pressure (P) of the mix is determined by the following equation.

$$P = p_{wg}x_w\gamma_w + p_{hg}(1-x_w)\gamma_h \quad (4)$$

where:
$p_{wg}$=Vapor pressure of water (mm Hg) (see equation below)
$x_w$=mole fraction of water
$p_{hg}$=Vapor pressure of hydrogen peroxide (mm Hg) (see equation below)
$\gamma_w$=Activity coefficient for water
The activity coefficient for water is determined by the following equation.

$$\gamma_w = \exp\left(\frac{(1-x_p)^2}{RT}[B_0 + B_1(1-4x_w) + B_2(1-2x_w)(1-6x_w)]\right) \quad (5)$$

where:
$x_p$=mole fraction of hydrogen peroxide
R=1.987 cal/gmole-K ideal gas constant
$B_0$=Coefficient for calculation of activity coeff.=−1017+0.97*T
$B_1$=Coefficient for calculation of activity coeff.=85
$B_2$=Coefficient for calculation of activity coeff.=13
T=Water vapor temperature (K)
The activity coefficient for hydrogen peroxide ($\gamma_h$) is determined by the following equation.

$$\gamma_h = \exp\left(\frac{(x_w)^2}{RT}[B_0 + B_1(3-4x_w) + B_2(1-2x_w)(5-6x_w)]\right) \quad (6)$$

The mole fraction of hydrogen peroxide ($x_p$) is determined by the following equation (taken from H2O2.com).

$$x_p = (\text{Percent}*MW_w)/(MW_p*(100-\text{Percent}) + \text{Percent}*MW_w) \quad (7)$$

where:
Percent=Percent hydrogen peroxide in gas or liquid form.
$MW_w$=Molecular weight of water=18.016 grams/mole.
$MW_p$=Molecular weight of hydrogen peroxide=34.016 grams/mole.

The vapor pressure of water is determined using the following equations (from the ASHRAE Fundamentals book). For temperatures above 32° F., the following equation is given:

$$VP = \text{Exp}[(C_8/(TF+460)] + C_9 + C_{10}*(TF+460) + C_{11}*(TF+460)^2 + C_{12}*(TF+460)^3 + C_{13}*\text{Log}(TF+460)) \quad (8)$$

where:
VP=Vapor pressure at saturation (psi)
TF=Vapor temperature (° F.)
$C_8$=−10440.397

$C_9 = -11.29465$
$C_{10} = -0.027022355$
$C_{11} = 0.00001289036$
$C_{12} = -2.4780681E-09$
$C_{13} = 6.5459673$

The vapor pressure of anhydrous hydrogen peroxide is determined by the following equation.

$$p_{hg} = 10^{\left(44.5760 - \frac{4025.3}{T} - 12.996 \log T + 0.0046055T\right)} \quad (9)$$

where:
$p_{hg}$=Vapor pressure of hydrogen peroxide (mm Hg)
T=Vapor temperature (K)

The ideal gas law can be used to calculate the saturation level of the hydrogen peroxide and water vapor components at a given temperature, as shown in reference 2. The ideal gas law is determined by the following equation.

$$PV = nRT \quad (10)$$

where:
P=Vapor pressure of water and peroxide mix (mm Hg).
V=Volume (m³)
n=Number of moles
R=Universal Gas Constant (0.082 liter-atm/mole-K)
T=Temperature of vapor (K)

The saturated concentration of peroxide or water vapor is usually given in mass per unit volume. Equation (10) can be arranged to determine concentration as given in equation (11) below.

$$C = w/V = Mn/V = MxP/(RT) \quad (11)$$

where:
C=Saturated Concentration of vapor (mg/liter)
w=Mass (mg)
V=Volume (liter)
M=molecular weight of water or hydrogen peroxide (grams/mole).
=34.016 grams/mole for peroxide
=18.016 grams/mole for water
x=Vapor mole fraction.
P=Vapor pressure of water and peroxide mix (mm Hg) from equations (8) and (9).
R=Universal Gas Constant (0.082 liter-atm/mole-K)
T=Temperature of vapor (K)

Equation (11) can be solved for the saturated concentration of water ($C_{w,sat}$) and hydrogen peroxide ($C_{h,sat}$). The percent of hydrogen peroxide vapor can be calculated using the following equation.

$$P_c = [C_{p,c}/(C_{p,c} + C_{w,c})]100 \quad (12)$$

where:
$P_c$=Percent hydrogen peroxide in vapor form.
$C_{p,c}$=Concentration of hydrogen peroxide from equation (11) (mg/liter)
$C_{w,c}$=Concentration of water from equation (11) (mg/liter)

The percent of hydrogen peroxide in vapor form calculated with equation (12) can be compared to the percent of hydrogen peroxide calculated using equations (1) and (2).

$$P = [C_p/(C_p + C_w)]100 \quad (13)$$

where:
P=Theoretical percent of hydrogen peroxide in air stream.
$C_p$ & $C_w$ are explained in equations (1) and (2) above.

The percent of peroxide calculated in equation (12) should match that calculated in equation (13). As explained above, if the percentage of hydrogen peroxide in the sterilant is used in equation (7), the percentage found using equation (12) will be too low. The equations can be forced to produce the correct saturated vapor concentration from equation (12) by increasing the concentration (Percent) of liquid hydrogen peroxide used in equation (7) until the concentration found using equations (12) and (13) match.

Inlet air temperature must be sufficient to vaporize the sterilant and provide an outlet temperature high enough to prevent condensation downstream. The required temperature at the inlet to the vaporizer tube is determined as follows.

The heat required to vaporize the hydrogen peroxide is mostly due to the latent heat of vaporization for the hydrogen peroxide. To a smaller extent, the sensible heat is needed to heat the liquid sterilant from room temperature to vaporization temperature. The heat of vaporization (latent heat) as a function of the concentration of hydrogen peroxide in water is given in FIG. 10, provided courtesy of H2O2.com.

The latent heat, $h_{fg}$, is given in units of calories per gram. The units for $h_{fg}$ can be converted to BTU per gram for 35% peroxide in water as follows.

$$h_{fg} = 525 \frac{cal}{gm}\left(\frac{1 \text{ BTU}}{251.9968 \text{ cal}}\right) = 2.083 \frac{BTU}{gm}$$

The heat of vaporization is determined by the following equation.

$$Q_{vap} = h_{fg}(I) \text{ (BTU/min)} \quad (14)$$

where:
I=sterilant injection rate (grams/min)

Figure 11:
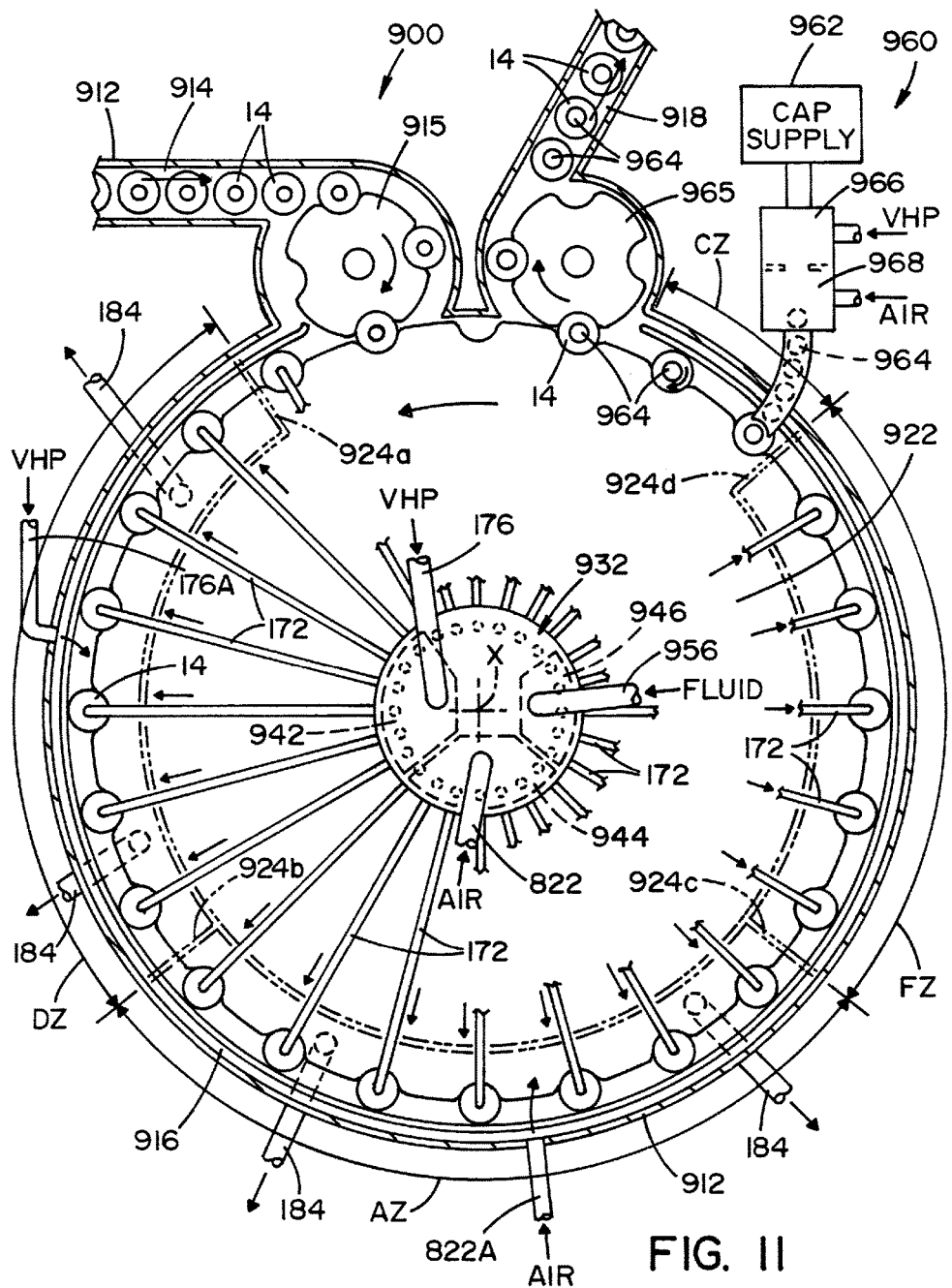
FIG. 11 is a sectioned, top plan view of a vaporized hydrogen peroxide decontamination system for decontaminating bottles and the like, illustrating another embodiment of the present invention.
Figure 12:
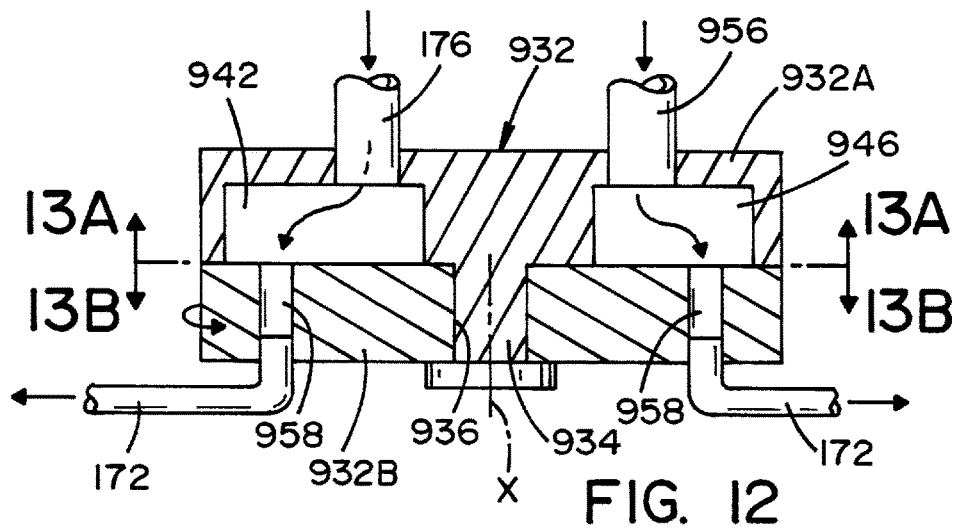
FIG. 12 is a sectional view of a rotary union that connects vaporized hydrogen peroxide, air and fluid inlet lines to injector connecting lines.

The sensible heat required to heat the sterilant from room temperature to the desired outlet temperature is determined by the following equation.

$$Q_{sen} = I \cdot \rho_{ster} \cdot C_{p,ster}(T_2 - T_{amb}) \quad (15)$$

where:
$\rho_{ster}$=density of the sterilant found from H2O2.com (see FIG. 11) (gram/ml)
$C_{p,ster}$=specific heat of sterilant found from H2O2.com (see FIG. 12) (BTU/gram-C)
$T_2$=vaporizer outlet temperature defined by user (C)
$T_{amb}$=ambient temperature of sterilant (C)
FIGS. 11 and 12 are provided courtesy of H2O2.com.

Hot air will be used to vaporize the sterilant. The heat lost by the air stream, $Q_{air}$, is determined by the following equation.

$$Q_{air} = \dot{m} C_p \cdot (T_1 - T_2) \text{ (BTU/min)} \quad (16)$$

where:
$\dot{m}$=air mass flow rate=(0.075 lbm/scf)×scfm (lbm/min)
$C_p$=specific heat of air at the bulk temperature (BTU/lbm-R)
$T_1$=inlet air temperature (into vaporizer tube) (° F.)
$T_2$=outlet air temperature (out of vaporizer tube) (° F.)

The outlet temperature is determined by knowing the dew point of the sterilant in the air stream using the equations given above. The value for $Q_{air}$ is equal to $Q_{vap}$ plus $Q_{sen}$. The only unknown in equation (16) is the inlet temperature. Solving equation (16) for $T_1$ gives:

$$T_1 = \frac{Q_{vap} + Q_{sen}}{\dot{m} \cdot C_p} + T_2 \quad (17)$$

Referring now to the operation of system 10, a controller (not shown) is programmed to allow system 10 to operate in three different modes of operation, namely: (1) operating to maintain a desired dew point temperature within decontamination chamber 100, (2) operating at a fixed rate of sterilant injection, and (3) operating so as to hold a desired peroxide concentration. The controller receives input signals from the various sensors throughout system 10. In addition, the controller is programmed, based upon the foregoing equations, to control the heating elements 498, 552, 852, blower motors 494, 522, 732, 812, and pump motors 324, 524, 628 in accordance with a selected mode of operation.

Referring first to the first mode of operation that maintains a specific dew point in the decontamination chambers, certain user inputs are required for this mode of operation. Specifically, the user inputs the following: (a) a desired dew point temperature ($T_{dp}$), (b) a desired vaporizer outlet temperature, and (c) the percent of hydrogen peroxide in the liquid sterilant.

When vaporized hydrogen peroxide sensor 674 is used, the dew point can be calculated. When no sensor is available, it may be estimated using equations (1) and (2) to calculate the water and peroxide concentrations (assuming efficiency is known).

As is known by those skilled in the art, a dew point temperature is the temperature at which water vapor or hydrogen peroxide vapor in the air becomes saturated and condensation begins. In the context of the present invention, the objective of system 10 when operated in the first mode of operation is to control the air temperature, air flow, and concentration of water and vaporized hydrogen peroxide (VHP) in the air stream so as to prevent condensation on bottles 14 to be sterilized. As will be appreciated by those skilled in the art, the temperature of bottles 14 to be sterilized is a factor in determining an actual dew point temperature. In the embodiment shown, bottles 14 are to be conveyed through decontamination chamber 100. The initial temperature of bottles 14 entering decontamination chamber 100 is important in determining the desired dew point temperature ($T_{dp}$). The desired dew point temperature is determined based upon the initial temperature of bottles 14 entering decontamination chamber 100. To ensure that condensation does not form on bottles 14, "the desired dew point temperature," also referred to as a "pre-selected temperature," inputted into the system is preferably a specific number of degrees lower than the initial temperatures of bottles 14 when entering decontamination chamber 100. In a preferred embodiment, the desired dew point temperature is selected to be approximately 30° C. lower than the initial temperature of bottles 14 when entering decontamination chamber 100. It will, of course, be appreciated that the added temperature factor could be increased or decreased, so long as it remains lower than the initial temperature of bottles 14.

As will be appreciated by those skilled in the art, the lower the temperature of bottles 14 to be sterilized when entering the decontamination chamber, the lower the dew point temperature at which the water or hydrogen peroxide vapor will condense on bottles 14.

The second piece of data inputted by the user is a desired vaporizer outlet temperature. To a certain extent, these data are also dependent on the physical properties of bottles 14 to be decontaminated. In this respect, it may be necessary to operate system 10 below a certain temperature to avoid damaging bottles 14.

The third piece of data inputted by the user is the percent of hydrogen peroxide in the liquid sterilant. This information is provided by the supplier of the liquid sterilant.

Based upon the foregoing inputted information, the system operates in the first mode of operation as follows.

Initially, both reservoir tanks 332A, 332B in sterilant supply unit 300 are preferably filled with liquid sterilant. Liquid sterilant is provided to the respective tanks by pump 322. Tanks 332A, 332B are preferably filled to a desired fill level, indicated by level sensor 354 in each tank 332A, 332B.

Preferably, one tank 332A or 332B is used to provide liquid sterilant to vaporizer unit 500 at any one time. Once a given tank 332A or 332B is depleted of liquid sterilant, liquid sterilant from the other tank 332A or 332B is then used to supply vaporizer unit 500. An empty tank 332A or 332B can be refilled by opening the appropriate valves 344, 346 to empty tank 332A or 332B and by pumping liquid sterilant from external supply 314 into the empty tank. While an empty tank 332A or 332B is being filled, the other tank 332A or 332B is used to supply vaporizer unit 500. Tanks 332A, 332B are dimensioned to allow continued operation of decontaminating system 10 while a tank 332A or 332B is being refilled. As a result, a generally continuous flow of sterilant can be provided simultaneously to vaporizer unit 500 to allow continuous processing of bottles 14.

As illustrated in FIG. 5, liquid sterilant from tanks 332A, 332B are directed to holding tank 370. Holding tank 370 is dimensioned to allow any gases that may have been released from the liquid sterilant to be vented from supply unit 300 prior to entering vaporizer unit 500. In this respect, it has been found that the outer dimensions of holding tank 370, being significantly larger than the feed lines and conduit in system 10, allows gas in the liquid sterilant to be released and vented, and prevents such gas bubbles or pockets from flowing to vaporizer unit 500.

As previously indicated, sterilant supply unit 300 is a gravity-feed system. To avoid trapping gas bubbles in vaporizer feed line 392, all conduit and piping forming vaporizer feed line 392 extending from holding tank 370 to vaporizer unit 500 have a downward slope such that any gas released by the liquid sterilant within vaporizer feed line 392 migrates to holding tank 370 where it can be released through vent line 374. Valve 376 in vent line 374 is controlled by float switch 377.

Referring now to the operation of vaporizer unit 500 as shown in FIG. 10, the controller of system 10 causes motor 524 to drive blower 522, thereby drawing air through the air-conditioning unit 400 and blowing the air into vaporizer 560 through vertical conduit 528. The air flow created by blower 522 is measured by flow element 532. As indicated above, motor 524 is preferably an electrically-controlled variable-speed motor wherein the air flow created through vaporizer 560 can be adjusted automatically by the controller. Heating element 552 is energized to heat the air entering vaporizer plenum 564. The output of heating element 552 may be adjusted by varying the duty cycle to heating element 552. In other words, the temperature of the air flowing into vaporizer plenum 564 can be adjusted by adjusting the output of heater element 552.

When system 10 is initially started up, air from blower 522 is forced through plenum 564 and through decontamination chamber 100. Heated air is blown through system 10 to allow components thereof to heat up until the temperature of system 10 stabilizes. Temperature sensors 474, 486, 536, 652, 654, 672, 726, 762 and 764 throughout system 10 monitor the temperature of the air within system 10 and determine when the system has reached an equilibrium temperature based upon the input temperature of heating element 552 as measured by temperature sensor 536.

Once the temperature of system 10 has stabilized, liquid sterilant is injected into the heated air stream by injector system 610. The amount of sterilant injected into the system is established by the controller based upon calculations using the equations set forth above. The initial injection of liquid sterilant into the heated stream creates a pressure increase within vaporizer plenum 564 as a result of the liquid sterilant vaporizing in the heated air stream. This increase in pressure within vaporizer plenum 564 will result in reduced air flow into vaporizer 560. This drop in air flow will be sensed by flow element 532. In accordance with one aspect of the present invention, the operation of blower 522 is controlled by the sensed air flow through flow element 532. Based upon output signals from flow element 532 and sensor 534, the controller increases the speed of blower 522 to maintain the desired air flow through vaporizer plenum 564 and the downstream units. In this respect, system 10 is self-adjusting to maintain a desired air flow rate through system 10 while vaporized hydrogen peroxide is being generated. The vaporized hydrogen peroxide from vaporizer unit 560 is conveyed into decontamination chamber 100 through vaporized hydrogen peroxide feed line 176. In accordance with another embodiment of the present invention, for safety reasons vaporizer unit 560 is located above decontamination chamber 100, as shown in FIG. 1. In this respect, any hydrogen peroxide not vaporized in vaporizer unit 560 will remain in a liquid state and drip or flow downward into decontamination chamber 100. The dripping or flowing of liquid hydrogen peroxide into decontamination chamber 100 may be ascertained from a visual inspection of decontamination chamber 100. If liquid hydrogen peroxide is noticed in decontamination chamber 100, the system is shut down to avoid a hazardous condition.

Referring now to the operation of system 10, bottles 14 are conveyed along entrance passageway 24 (see FIG. 1). As best seen in FIG. 2, a bottle 14 is received within a recess 36 in first inlet rotary transfer device 32A. First inlet rotary transfer device 32A transfers bottle 14 into decontamination chamber 100 and into a recess 118 that is formed in the periphery of plate 116. As best seen in FIG. 3, bottle 14 rests upon turntable 112 and within recess 118 of plate 116. Rotation of turntable 112 about axis "A" causes the bottles to move along a circular path through decontamination chamber 100, as illustrated in FIG. 2. FIG. 3 illustrates the position of injector 162, as bottle 14 enters decontamination chamber 100. The vaporized hydrogen peroxide (VHP) enters decontamination chamber 100 through feed line 176. The VHP flows through rotary union 182 into distribution block 174. From distribution block 174, the VHP is fed through the plurality of connector hoses 172 that connect distribution block 174 to each of the injectors 162. In this respect, VHP flows through connector hoses 172 through opening 168 in slide 142 to passageway 164 in injector 162. The VHP is dispensed from the orifice 166 of injector 162, as illustrated by the arrows in FIG. 3. In this respect, as a bottle 14 enters decontamination chamber 100, VHP is being dispensed from injector 162 above the throat of bottle 14, as illustrated in FIG. 3. The VHP from each of the injectors 162 basically fills decontamination chamber 100 with vaporized hydrogen peroxide (VHP). As turntable 112 rotates about axis "A," roller 148 on slide 142 follows guide slot 154 in guide plate 152. Guide slot 154 is formed to form a continuous path from the upper edge of guide plate 152 to the lower edge of guide plate 152 such that slide 142 is caused to move downwardly along guide rod 136 as roller 148 follows guide slot 154. FIG. 4 shows the position of injector 162 when slide 142 is at its lowermost position relative to guide rod 136. As illustrated in FIG. 4, the vaporized hydrogen peroxide (VHP) that exits injector 162 is forced into the interior of bottle 14 and up out through the throat of the bottle around injector 162. In this respect, vaporized hydrogen peroxide (VHP) is injected directly into the interior of the bottle to ensure that all surfaces therein are exposed to the vaporized hydrogen peroxide (VHP). As the bottle moves around the circular path within decontamination chamber 100, guide slot 154 is designed to cause slide 142 to move upwardly along guide rod 136 to withdraw injector 162 from bottle 14 as bottle 14 approaches the exit of decontamination chamber 100. First outlet rotary transfer device 32B conveys each bottle 14 from turntable 112 to connecting passageway 42 (see FIG. 2). VHP injected into decontamination chamber 100 is removed from decontamination chamber 100 by one or more VHP outlet lines 184 connected to decontamination chamber 100. A VHP outlet line 184 is also connected to connecting passageway 42 to withdraw vaporized hydrogen peroxide (VHP) therefrom. VHP withdrawn from decontamination chamber 100 and connecting passageway 42 is connected to destroyer unit 700. Bottles 14 in connecting passageway 42 are conveyed into aeration chamber 200 by second inlet rotary transfer device 62A. Each bottle is transferred to a turntable that in the embodiment shown is the same as the turntable described above with respect to decontamination chamber 100. Aeration chamber 200 includes an assembly for aerating bottles 14 that in the embodiment shown is the same as assembly 110 for decontaminating bottles in decontamination chamber 100. In this respect, bottles are conveyed along a circular path within aeration chamber 200 and an injector injects clean, filtered air from aeration unit 800 into bottles 14, as schematically illustrated in FIG. 1. In this respect, each bottle includes an associated injector that is mounted to a slide that in turn is movable along a guide rod in the same fashion as previously described with respect to decontamination chamber 100. Rather than injecting VHP, in aeration chamber 200, clean, filtered air is conveyed to each injector from connector hoses 172. In the same fashion as previously described, the clean, filtered air blown through the injectors within aeration chamber 200, blow clean, filtered air around the body and into aeration chamber 200. As illustrated in FIG. 3, clean, filtered air is blown into aeration chamber 200 (which is marked as decontamination chamber 100 in FIG. 3) above bottle 14 as a bottle is conveyed along a circular path by turntable 112, the injector is inserted into bottle 14 as illustrated in FIG. 4. Air is blown into bottle 14 to force any residual VHP gas that may remain therein out through the neck of the bottle around injector 162. The injector forces clean dry air into the bottle to force any residual VHP therefrom. Bottles 14 then exit aeration chamber 200 by means of second outlet rotary transfer device 62B that transfers the bottles from turntable 112 to exit passageway 52, wherein the bottles are conveyed along a processing line for filling (not shown).

The present invention thus provides a continuous processing line for decontaminating bottles prior to a filling process. Like turntables and injector assemblies are used in both decontamination chamber 100 and aeration chamber 200.

According to one aspect of the present invention, the concentration of vaporized hydrogen peroxide (VHP) within the decontamination chamber is monitored by sensors within the decontamination chamber and by controlling the flow through the decontamination chamber. In this respect, the flow of vaporized hydrogen peroxide (VHP) into and out of the decontamination chamber is controlled by the flow of VHP entering the chamber through injectors 162 and by the flow of VHP out of the chamber through one or more VHP outlet lines 184.

Similarly, air flow through aeration chamber 200 is controlled by controlling the air flow to injectors 162 in aeration chamber 200 and by controlling the air flow out of aeration chamber 200 through one or more air outlet lines 186 connected to the interior of aeration chamber 200.

As schematically illustrated in the drawings, the vaporized hydrogen peroxide is directed over bottles 14 from above. As illustrated in FIG. 9, blower 732 in destroyer unit 700 is energized to draw the vaporized hydrogen peroxide out of decontamination chamber 100 through VHP outlet line 184. Flow element 722 provides signals indicative of the flow to blower 732. The controller controls the operation of blower 732 so as to balance the air flow out of decontamination chamber 100 with the flow of air through vaporizer plenum 564. The air stream drawn from decontamination chamber 100 is forced through destroyer 742 where the vaporized hydrogen is broken down into oxygen and water that is exhausted from system 10, as schematically illustrated in FIG. 1.

As indicated above, during this mode of operation, i.e., wherein the system is controlled to maintain the concentration of water vapor and vaporized hydrogen peroxide in decontamination chamber 100 at a desired level for a desired operating temperature, the controller of system 10 constantly monitors the various sensors throughout system 10 to ensure that the proper amount of liquid hydrogen peroxide sterilant is being injected into injection system 610.

In accordance with another aspect of the present invention, system 10 monitors and verifies the amount of vaporized hydrogen peroxide produced within system 10 in several ways. According to a first method of measuring the vaporized hydrogen peroxide (VHP), system 10 monitors the temperature drop across destroyer 742 using temperature sensors 762 and 764. In this respect, the destruction of vaporized hydrogen peroxide produces heat. By monitoring the change in temperature across destroyer 742, a first indication of the amount of vaporized hydrogen peroxide flowing through the system can be determined.

A second method of measuring and monitoring the concentration of vaporized hydrogen peroxide within system 10 is through measurements from vaporized hydrogen peroxide sensor 662 (see FIG. 10) or 674 (see FIG. 1).

A third method of measuring and monitoring the amount of vaporized hydrogen peroxide in system 10 is by monitoring the injection rate of liquid sterilant into injection system 610 (see FIG. 10). In this respect, the output of mass meter 627 (see FIG. 6) can be monitored to provide an indication of the metered amounts of liquid sterilant sent to injection system 610. The peroxide and water concentrations are calculated using equations 1 and 2.

A fourth method of measuring and monitoring the amount of vaporized hydrogen peroxide in system 10 is to monitor the temperature change within vaporizer plenum 564 (see FIG. 10). Specifically, temperature sensors 652 and 654 within vaporizer plenum 564 are monitored. Just as the destruction of vaporized hydrogen peroxide produces a specific amount of heat per unit mass, so, too, does the vaporization of liquid hydrogen peroxide require a specific amount of heat which produces a decrease in temperature. By monitoring the change in temperature in the air stream within vaporizer plenum 564, the amount of vaporized hydrogen peroxide in system 10 can be determined.

In accordance with one aspect of the present invention, system 10 monitors all four of the foregoing conditions and compares the output calculations to each other. If any one of the four monitored parameters is outside an acceptable range of error, system 10 alerts the system operator of potential problems.

By continuously monitoring the sensors throughout system 10, the concentration of water vapor and hydrogen peroxide vapor within the air stream can be maintained at a desired level for a desired operating temperature. Since, as indicated above, the desired operating dew point temperature is preferably approximately 30° C. below the temperatures of bottles 14 entering the decontamination chamber, condensation on such bottles 14 can be avoided.

The present invention thus provides a system 10 that can operate to maintain a specific dew point temperature, to prevent water vapor or vaporized hydrogen peroxide from condensating on bottles 14 and, at the same time, maintain a desired operating temperature so as not to damage bottles 14 to be decontaminated.

Referring now to the second mode of operation, i.e., wherein system 10 is held to a predetermined injection rate, the user is required to once again input into the controller of a system 10 a desired temperature that system 10 should maintain within decontamination chamber 100, and the percent of hydrogen peroxide in the liquid sterilant. In this mode of operation, once a steady-state flow has been established, the injection rate of injection system 610 (see FIG. 10) is maintained at a set amount. Air flow through the system may increase to maintain a desired operating temperature, however, the injection rate remains constant throughout the operation in this mode. The dew point is supplied to the user so a determination can be made if condensation will occur.

In the third mode of operation, i.e., wherein the vaporized hydrogen peroxide concentration is held steady, the user inputs into the controller of system 10 a desired operating temperature that system 10 should maintain within decontamination chamber 100. Once steady-state air flow has been established through the system, liquid hydrogen peroxide is injected into the air stream. As indicated above, system 10 monitors the amount of vaporized hydrogen peroxide in system 10 and maintains the desired vaporized hydrogen peroxide concentration by increasing or decreasing the injection rate of pump 626 (see FIG. 6) of injection system 610 (see FIG. 10).

The control strategy for the first mode of operation is carried out as follows:

1.) The user inputs the following:
   a. The desired dew point temperature ($T_{dp}$)
   b. The manifold temperature.
   c. The percent hydrogen peroxide in the liquid sterilant
2.) The following is known:
   a. Vaporizer efficiency (E) found through testing. (When a near IR sensor 662 (see FIG. 10) is used, equations 1 and 2 are not required to determine the concentrations of hydrogen peroxide and water. When a near IR sensor 662 is not used, equations 1 and 2 are used to calculate the concentrations of hydrogen peroxide and water. This calculation requires that the efficiency of the vaporizer be inputted by the user into the controller of system 10.)
   b. Concentration of water in the air stream out of the dryer, from vendor data or from testing.
3.) Initially assume the vapor out of the vaporizer will contain the same percentage of hydrogen peroxide as the liquid sterilant.
4.) Calculate the mole fraction of hydrogen peroxide ($x_p$) in the sterilant using equation 7.

Figure 13A:
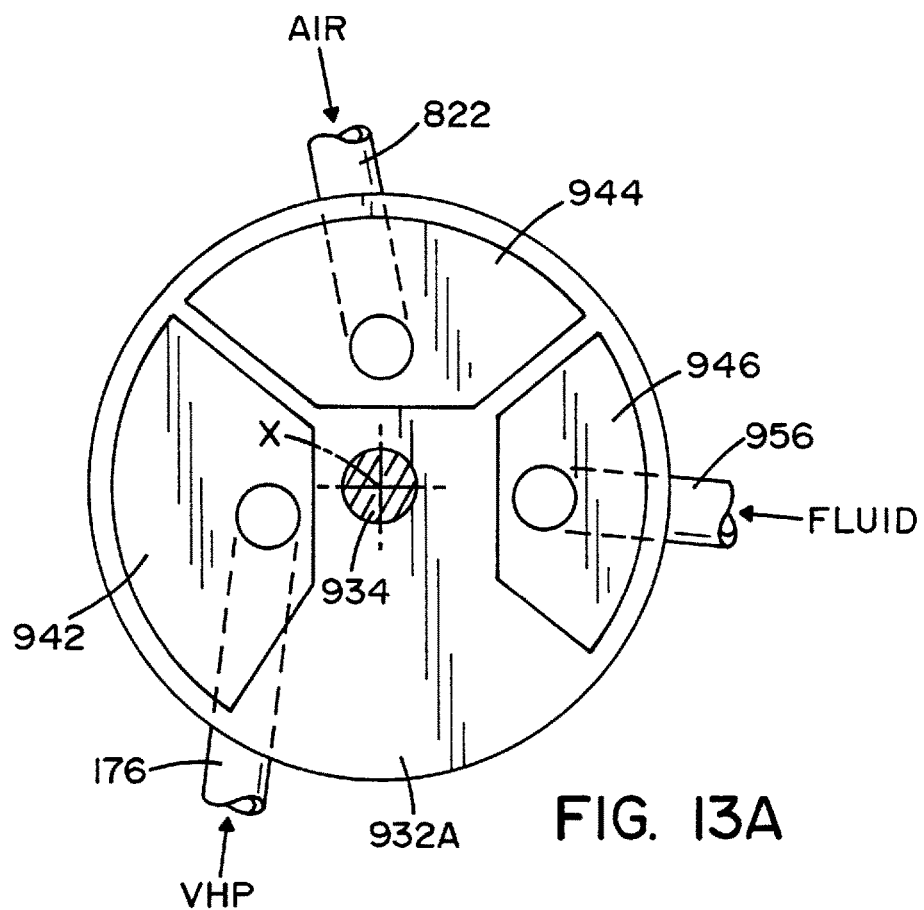
FIG. 13A is a view taken along lines 13A-13A of FIG. 12.
Figure 13B:
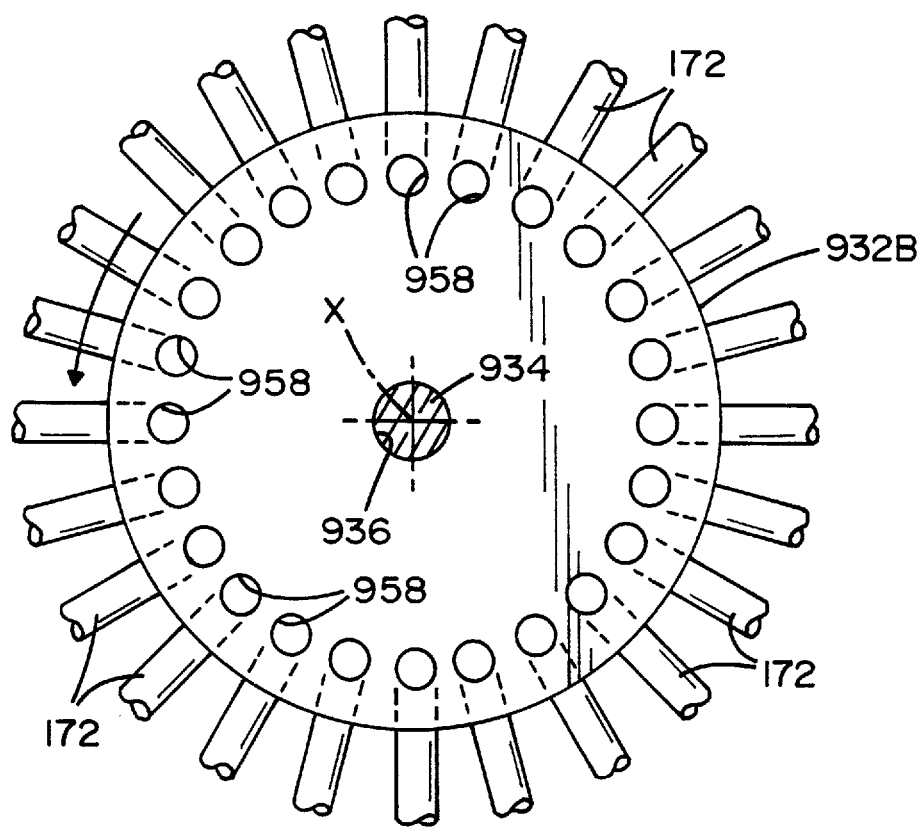
FIG. 13B is a view taken along lines 13B-13B of FIG. 12.

5.) Calculate the mole fraction of water in the sterilant, $x_w = 1 - x_p$
6.) Calculate the activity coefficients using equations 5 and 6 at the dew point temperature input by the user.
7.) Calculate the vapor pressure of water and hydrogen peroxide using equations 8 and 9 at the dew point temperature input by the user.
8.) Calculate the total vapor pressure using equation 4.
9.) Determine the mole fraction of hydrogen peroxide in gas over liquid using equation 3.
10.) Determine if the mole fraction calculated using equation 7 equals that calculated using equation 3.
11.) If the mole fractions don't match within an acceptable error, iterate the mole fraction of peroxide in the sterilant (liquid state) and redo steps 5 through 10 above. One of many iteration techniques may be used to converge to the solution.
12.) If the mole fractions match within the acceptable error, calculate the saturated concentration of the hydrogen peroxide ($C_{h,sat}$) and water ($C_{w,sat}$) using equation 11.
13.) Calculate the sterilant injection rate from equation 1 using $C_{h,sat}$.
14.) Calculate the concentration of water ($C_w$) using equation 2.
15.) Compare $C_w$ with $C_{w,sat}$
16.) If $C_w$ and $C_{w,sat}$ are not equal within an acceptable error, recalculate the percentage of peroxide (P) using $C_{h,sat}$ and $C_w$: $P = C_{h,sat}/(C_{h,sat} + C_w) \cdot 100$ and redo steps 4 through 15.
17.) If $C_w$ and $C_{w,sat}$ are within acceptable error, the initial injection rate will be set equal to that calculated in step 15 above.
18.) Calculate the heat of vaporization ($Q_{vap}$) using equation 14.
19.) Determine the vaporizer inlet air temperature ($T_1$) using equation 16.
20.) If the air temperature calculated in step 19 is not too great for downstream components, the air flow can be established at $T_1$ and the peroxide can be injected into the air stream after the system has reached steady state.
21.) If the air temperature, $T_1$ is too great for downstream components, the temperature may be initially set to the maximum allowable temperature.

22.) The injection rate can then be determined by iterating until the vaporizer outlet temperature is above the dew point by the same margin as that between the desired dew point temperature ($T_{dp}$) and the desired outlet temperature ($T_2$).

23.) A gradual step-up process can be continued until the required dew point ($T_{dp}$) and outlet ($T_2$) temperatures are achieved.

24.) If feedback is provided to the control, the dew point can be achieved by using the actual concentration of hydrogen peroxide and water instead of those calculated in equations 1 and 2.

The control strategy for the second mode of operation is set forth as follows.

1.) The user inputs the following:
   a. The desired injection rate
   b. The manifold temperature.
   c. The percent hydrogen peroxide in the liquid sterilant 2.) The following is known:
   a. Vaporizer efficiency (E) found through testing (used when near IR sensor is not used).
   b. Concentration of water in the air stream out of the dryer, from vendor data or from testing.

3.) The controller calculates and displays a dew point based upon the injection rate set by the user.

4.) The user, knowing the dew point for the inputted injection rate, can then, if necessary, adjust, i.e., change, the "user inputs" to avoid condensation on the articles to be decontaminated. In this respect, in the second mode of operation, there is no automatic control of the dew point.

The control strategy for the third mode of operation is set forth as follows.

1.) The user inputs the following:
   a. The desired concentration of hydrogen peroxide.
   b. The manifold temperature.
   c. The percent hydrogen peroxide in the liquid sterilant.

2) The following is known:
   1) Vaporizer efficiency (E) found through testing (used when near IR sensor is not used).
   2) Concentration of water in the air stream out of the dryer, from vendor data or from testing.

3) The controller calculates and steps-up the injection rate of the liquid hydrogen peroxide until the desired concentration of vaporized hydrogen peroxide is achieved.

4) The controller calculates and displays the dew point at desired concentration of hydrogen peroxide.

Referring now to FIGS. 11-13B, a bottling system 900 illustrating an alternate embodiment of the present invention is shown. Unlike the prior embodiment wherein a decontamination chamber 100 and a separate aeration chamber 200 are shown as part of bottling system 10, in system 900 a bottle 14 is sterilized, aerated, filled and capped on a single turntable mechanism. System 900 includes an outer housing 912 that defines an entrance passageway 914, a generally cylindrical interior chamber 916 and an exit passageway 918. Interior chamber 916 is dimensioned to contain a turntable 922 that is essentially the same as that disclosed in FIGS. 1-10, but larger to accommodate more bottles 14. As in the prior embodiment, turntable 922 is designed to convey bottles 14 along a circular path from the entrance passageway 914 to exit passageway 918. In accordance with the embodiment shown, bottles 14 are sterilized, aerated, filled with a fluid and capped between entrance passageway 914 and exit passageway 918. As in the prior embodiment, system 900 includes injector assemblies that are essentially the same as that shown in FIGS. 3 and 4, wherein injector 162 (not shown in FIGS. 11-13B) may be guided into and out of bottle 14 by means of a slide 142 moving along guide rod 136. In system 900, bottle 14 passes through a decontamination zone "DZ," an aeration zone "AZ," a filling zone "FZ" and a capping zone "CZ." The foregoing zones are defined by baffles 924*a*, 924*b*, 924*c*, 924*d* (shown in phantom lines in FIG. 11) that are formed along the path of bottles 14. Baffles 924*a*, 924*b*, 924*c* and 924*d* each have an opening (not shown) therethrough that allow bottles 14 and injectors 162 to pass therethrough with minimum clearance as is conventionally known.

In the embodiment shown, each injector 162 is connected by a slide 142 to a connector hose 172 that connects injector 162 to a distribution block 932, best seen in FIG. 12. Distribution block 932, best seen in FIG. 12, is comprised of an upper stationary section 932A and a lower rotating section 932B. Upper section 932A and lower section 932B have planar surfaces that mate with each other and allow upper section 932A and lower section 932B to move relative to each other. In the embodiment shown, a cylindrical pin 934 extending from the planar surface of upper section 932A is received in a cylindrical bore 936 in lower section 932B to facilitate rotational movement between upper section 932A and lower section 932B about an axis, designated "X" in FIG. 12. Three (3) isolated cavities 942, 944, 946, best seen in FIG. 13A, are formed in upper section 932A to define three (3) chambers when upper section 932A is mated with lower section 932B. A vaporized hydrogen peroxide feed line 176 from vaporizer unit 500 communicates with a first cavity 942 to define a VHP chamber. An aeration conduit 822 from aeration unit 800 communicates with second chamber 944 to define an air cavity. A fluid, i.e., product, inlet line 956 communicates with third cavity 946. Lower section 932B of distribution block 932 includes a plurality of equally spaced apertures 958 that are arranged symmetrically about central axis "X." Each aperture 958 is connected to a connector hose 172, as best seen in FIGS. 12 and 13B.

As best seen in FIG. 11, first cavity 942 in upper section 932A of distribution block 932 defines the decontamination zone "DZ" within interior chamber 916 of housing 912. Second cavity 944 in distribution block 932 defines aeration zone "AZ" of interior chamber 916. Third cavity 946 defines filling zone "FZ."

A capping station 960 is provided at the end of filling zone "FZ," as schematically illustrated in FIG. 11. In the embodiment shown, a supply of caps 962 provide caps 964 aligned along a path that intersects a path of bottles 14 moving along turntable 922. Caps 964 pass through a decontamination chamber 966 wherein VHP from vaporizer unit 500, as heretofore described, is conveyed over caps 964 to decontaminate the same. Caps 964 pass into an aeration chamber 968 where air from the aforementioned aeration unit 800 removes residual VHP from caps 964. Sterilized caps 964 are then conveyed to a bottle capping mechanism (not shown) that caps bottles 14 moving along turntable 922. As indicated above, bottling system 900 is designed for use in conjunction with a high-capacity VHP generating system as described above wherein a single, high-capacity VHP vaporizer unit 500 generates sufficient VHP to sterilize bottles 14 continuously moving along bottling system 900. In this respect, bottling system 900 includes a sterilant supply unit 300, an air conditioning unit 400, a vaporizer unit 500, a destroyer unit 700 and an aeration unit 800, as heretofore described.

Referring now to the operation of system 900, bottles 14 are conveyed and aligned along entrance passageway 914 and are conveyed by intermediate conveyor 915 to turntable 922. The bottles 14 are captured within the recesses of the turntable and are conveyed along the circular path through the interior chamber 916 of housing 912. As each bottle 14 passes past baffle 924a that defines the entrance to decontamination zone DZ, the connector hose 172 associated with an injector 162 above a bottle 14 becomes aligned with first chamber (cavity) 942 in distribution block 932. VHP fed from vaporizer unit 500 through vaporized hydrogen peroxide feed line 176 is forced into first chamber 942 and through connector hoses 172 that communicate with first chamber 942. In other words, as bottle 14 passes through the decontamination zone DZ, VHP is conveyed from vaporizer unit 500 through first chamber 942 and through the associated connector hose 172 into and around bottles 14 in decontamination zone DZ, thereby filling bottles 14 with vaporized hydrogen peroxide. As with the previous embodiment, VHP exiting bottle 14 likewise flows around the exterior of bottle 14 thereby decontaminating the entire bottle surface. An auxiliary VHP line 176A shown in FIG. 11 is provided to provide additional VHP to the decontamination zone DZ to ensure sterilization of the exterior of bottles 14. Outlet lines 184 communicate with decontamination zone DZ to exhaust VHP from the decontamination zone DZ and convey it to destroyer unit 700. As described above, system 900 monitors and controls the flow of VHP through decontamination zone DZ to ensure a specific amount of VHP within decontamination zone DZ as bottles 14 move therethrough.

Eventually, bottles 14 pass through baffle 924b that separates decontamination zone DZ from aeration zone AZ. At the same time, apertures 958 in lower section 932B of distribution block 932 that are associated with connector hoses 172 that are in turn associated with injectors 162 within bottles 14, move into communication with second chamber 944 of distribution block 932 wherein dry, clean, filtered air from aeration unit 800 is forced through connector hose 172 and through injector 162 into bottles 14. As a bottle moves through aeration zone AZ, clean, dry, filtered air is continually forced into bottle 14 to force residual VHP therefrom. At the same time, an auxiliary air inlet line 822A is connected to aeration zone AZ to force additional clean, dry, filtered air into aeration zone AZ to remove VHP around bottles 14. Outlet lines 184 communicating with aeration zone AZ exhaust air and residual VHP from aeration zone AZ to destroyer unit 700. The combination of air being forced into and around bottles 14 through injectors 162 and air inlet lines 822, 822A and the air being drawn out through outlet lines 184 creates an air flow through aeration zone AZ to remove residual VHP from and around bottles 14 from the time a bottle 14 reaches baffle 924c between aeration zone AZ and filling zone FZ. As a bottle 14 passes baffle 924c, apertures 958 in lower section 932B of distribution block 932 pass from second chamber 944 to third chamber 946 which is filled with a fluid, i.e., the product. In this respect, bottles 14 are then filled with a fluid as they pass through filling zone FZ of bottling system 900. In this respect, the flow of fluid into third chamber 946 and into bottles 14 is preferably controlled such that bottles 14 are filled to an appropriate level when they reach the end of filling zone FZ. It would of course be appreciated that other means of controlling flow into bottles 14 could be provided when filling the bottles.

Once a bottle 14 is filled and passes through baffle 924d defining the end of filling zone FZ, it intersects the cap pathway, wherein a sterilized cap 964 is applied to a bottle 14 and secured thereto by conventional capping means (not shown). The filled and capped bottle 14 is then conveyed by an intermediate conveyor 965 from turntable 922 to exit passageway 918 where the filled and capped bottle 14 then proceeds to stacking and storage.

The embodiment shown in FIGS. 11-13 illustrates an alternate embodiment wherein a single VHP generating system is used in conjunction with a single bottling system to perform both sterilization and aeration on the same turntable, where filling and capping may also occur using the same turntable.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A method of sterilizing at least one bottle, said method comprising the steps of:

moving said bottle continuously along a path, a first portion of the path being defined by a decontamination chamber, an outer boundary of the decontamination chamber being at least partially defined by a portion of a housing, the portion of the housing at least partially surrounding the decontamination chamber, said portion of the housing comprising a guide plate mounted to and extending about a circumference of an inner surface of said portion of the housing, said guide plate having a generally continuous slot formed therein as a continuous path from an upper edge of the guide plate to a lower edge of the guide plate, said bottle having an interior;

providing a source of a gaseous sterilant of a known concentration;

providing an assembly for distributing a predetermined amount of said gaseous sterilant from said source of said gaseous sterilant to said bottle when said bottle is disposed along the first portion of said path, said assembly being configured to support said bottle, said assembly including a center hub of said decontamination chamber, said center hub being positioned at a center of said decontamination chamber and being rotatable about a vertical axis, said assembly further comprising a circular plate secured to said center hub, the circular plate having at least one recess disposed along a peripheral edge thereof, said recess being dimensioned to receive an outer diameter of said bottle, said assembly further including at least one guide rod connected to said circular plate and associated with the recess, said assembly further including at least one slide mounted on the guide rod and configured to reciprocally move along the guide rod, the slide having a roller that is movable through said slot to cause said slide to reciprocally move along said guide rod, said assembly further comprising at least one injector associated with said at least one bottle, said injector being attached to the slide, said injector being fluidly connected to said source of gaseous sterilant, said injector being configured to move with said bottle received in the recess, said slide being configured to move said injector between a first position at which said injector is disposed above said bottle and a second position at which said injector is disposed within said interior of said bottle;

moving said bottle into a beginning of said first portion of said path at which said bottle is moved into said recess of said circular plate, said injector being in said first position when said bottle is moved into said recess;

dispensing said gaseous sterilant through said injector when said bottle is moved into said beginning of said first portion of said path, thereby filling said decontamination chamber with said gaseous sterilant and exposing an outer surface of said bottle to said gaseous sterilant; and rotating said bottle along said first portion of said path about said vertical axis from said beginning of said first portion of said path toward an end of said first portion of said path, the rotating causing said roller on said slide to follow said slot in said guide plate, thereby resulting in said slide moving downwardly along said guide rod when said slot moves toward said lower edge of said guide plate, said downwardly moving slide moving from said first position into said second position, thereby forcing said gaseous sterilant being dispensed through said injector into said interior of said bottle such that said gaseous sterilant forced into said interior of said bottle exits the interior of said bottle through a throat of the bottle to an area along said outer surface of said bottle, wherein, after said slide reaches said second position, as said bottle continues to be rotated toward said end of said first portion of said path, said slide moves upwardly along said guide rod when said slot moves toward said upper edge of said guide plate, thereby upwardly moving slide from said second position into said first position.

2. A method as defined in claim 1, further comprising:

moving said bottle from said end of said first portion of said path in said decontamination chamber to a second portion of said path in an aeration chamber at least partially defined by a second portion of the housing, said assembly being a first of a plurality of assemblies, a second of said assemblies being configured to distribute a predetermined amount of dry, filtered air from a source thereof to said bottle when said bottle is disposed along the second portion of said path, said at least one injector being a first of a plurality of said at least one injectors associated with said at least one bottles;

fluidly connecting a second of said injectors associated with said bottle to a source of a dry, filtered air when said bottle associated with said second injector is disposed along said second portion of said path; and conveying said dry, filtered air through said second injector and into said interior of said bottle when said bottle is disposed along said second portion of said path.

3. A method as defined in claim 1, wherein said first portion of said path defines a decontamination zone and said assembly includes an auxiliary line that fluidly connects said decontamination zone to said source of said gaseous sterilant, and wherein said dispensing includes dispensing said predetermined amount of said gaseous sterilant through said auxiliary line and through said decontamination zone.

* * * * *